US007414173B1

(12) United States Patent
Herrmann et al.

(10) Patent No.: US 7,414,173 B1
(45) Date of Patent: Aug. 19, 2008

(54) ISOLATED NUCLEIC ACID MOLECULES ENCODING ORALLY ACTIVE ANDROCTONUS AMOREUXI PESTICIDAL BIOPEPTIDES

(75) Inventors: Rafael Herrmann, Wilmington, DE (US); Albert L. Lu, Newark, DE (US); Billy F. McCutchen, Clive, IA (US); James K. Presnail, Avondale, PA (US); James F. H. Wong, Johnston, IA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 652 days.

(21) Appl. No.: 10/617,978

(22) Filed: Jul. 11, 2003

Related U.S. Application Data

(60) Provisional application No. 60/395,428, filed on Jul. 12, 2002.

(51) Int. Cl.

| | |
|---|---|
| *A01H 5/00* | (2006.01) |
| *A01H 5/10* | (2006.01) |
| *C12N 15/82* | (2006.01) |
| *C12N 15/12* | (2006.01) |
| *C07K 14/435* | (2006.01) |

(52) U.S. Cl. ................... 800/302; 536/23.5; 435/235.1; 424/93.2; 800/287; 800/320.2; 800/279

(58) Field of Classification Search ....................... None
See application file for complete search history.

(56) References Cited

U.S. PATENT DOCUMENTS

| | | | |
|---|---|---|---|
| 5,177,308 | A | 1/1993 | Barton et al. |
| 5,689,043 | A | 11/1997 | Broekaert et al. |
| 6,127,336 | A | 10/2000 | Bulet et al. |

FOREIGN PATENT DOCUMENTS

| | | | |
|---|---|---|---|
| WO | WO 93/05153 | | 3/1993 |
| WO | WO 97/30082 | | 8/1997 |
| WO | WO 99/09189 | | 2/1999 |
| WO | WO 00/24772 | | 5/2000 |
| WO | WO 00/32777 | | 6/2000 |
| WO | WO 00/78957 | | 12/2000 |
| WO | WO 00/78958 | | 12/2000 |
| WO | WO0078957 | * | 12/2000 |
| WO | WO 03/028666 | * | 4/2003 |

OTHER PUBLICATIONS

Inceoglu et al, 2001, Eur. J. Biochem. 268:5407-5413.*
Guo et al, 2004, Proc. Natl. Acad. Sci. USA 101: 9205-9210.*
Lazar et al, 1988, Mol. Cell. Biol. 8:1247-1252.*
Hill et al, 1998, Biochem. Biophys. Res. Comm. 244:573-577.*
Zeng et al, 2006, Peptides 27:1745-1754.*
Bin, Y., et al., "Insect-Resistant Tobacco Plants Expressing Insect-Specific Neurotoxin AaIT," *Chinese Journal of Biotechnology*, 1996, pp. 67-72, vol. 12(2).
Broekaert, W.F., et al., "Antimicrobial Peptides from Plants," *Critical Reviews in Plants Sciences*, 1997, pp. 297-323, vol. 16(3).
Gao, A., et al., "Fungal Pathogen Protection in Potato by Expression of a Plant Defensin Peptide," *Nature Biotechnology*, 2000, pp. 1307-1310, vol. 18.
Lapied, B., et al., "Biophysical Properties in Scorpion α-Toxin-Sensitive Background Sodium Channel Contributing to the Pacemaker Activity in Insect Neurosecretory Cells (DUM Neurons)," *European Journal of Neuroscience*, 1999, pp. 1449-1460, vol. 11.
Pang, S., et al., "Expression of a Gene Encoding a Scorpion Insectotoxin Peptide in Yeast, Bacteria and Plants," *Gene*, 1992, pp. 165-172, vol. 116.
Stewart, L.M.D., et al., "Construction of an Improved Baculovirus Insecticide Containing an Insect-Specific Toxin Gene," *Nature*, 1991, pp. 85-88, vol. 352.
Zlotkin, E., et al., "AaIT: From Neurotoxin to Insecticide," *Biochimie*, 2000, pp. 869-881, vol. 82.
Zlotkin, E., et al., "Oral Toxicity to Flesh Flies of a Neurotoxic Polypeptide," *Archives of Insect Biochemistry and Physiology*, 1992, pp. 41-52, vol. 21.
Inceoglu, B., et al.., "Isolation and Characterization of a Novel Type of Neurotoxic Peptide from the Venom of the South African Scorpion *Parnbuthus transvaclicus* (Bulhidae)," *Eur. J. Biochem*, 2001, pp. 5407-5413, vol. 268.

* cited by examiner

*Primary Examiner*—Anne R Kubelik
(74) *Attorney, Agent, or Firm*—Alston & Bird LLP

(57) ABSTRACT

The present invention provides compositions and methods for isolated nucleic acid molecules encoding orally active *Androctonus amoreuxi* pesticidal polypeptides. Compositions include novel nucleotide sequences encoding *Androctonus amoreuxi* pesticidal polypeptides, and biologically active variants thereof. Further provided are methods for modulating the pesticide resistance of plants using the nucleotide sequences disclosed herein. One method comprises stably transforming into the genome of a plant cell a nucleotide sequence of the present invention operably linked to a heterologous promoter and regenerating a stably transformed plant that expresses the nucleotide sequence. An additional method comprises incorporating a nucleotide sequence of the present invention operably linked to a heterologous promoter into a microorganism and applying said microorganism to the environment of a plant.

33 Claims, 14 Drawing Sheets

ISOLATED NUCLEIC ACID MOLECULES ENCODING ORALLY ACTIVE ANDROCTONUS AMOREUXI PESTICIDAL BIOPEPTIDES

CROSS-REFERENCE TO RELATED APPLICATION

This application claims the benefit of U.S. Provisional Application No. 60/395,428, filed Jul. 12, 2002, which is hereby incorporated herein in its entirety by reference.

FIELD OF THE INVENTION

The present invention relates to naturally occurring pesticides, in particular, to polypeptides isolated from arthropods. The invention further relates to methods of impacting pests, particularly insect pests, involving the pesticidal polypeptides and the corresponding nucleic acid molecules that encode the pesticidal polypeptides.

BACKGROUND OF THE INVENTION

Chemical insecticides are an integral component of modern agriculture, and are an effective means for reducing crop damage by controlling insect pests. However, chemical agents are under continuous scrutiny due to the potential for environmental contamination, selection of resistant populations of agronomic pests, and toxicity to non-target organisms such as beneficial insects, aquatic organisms, animals and humans. As a result, alternative strategies for insect control are being sought that are effective and yet benign to non-target populations and the environment. One of these strategies is to utilize the mechanisms of naturally occurring pathogens of target pest populations.

Examples of this type of strategy include the use of various forms of the δ-endotoxin produced by the soil dwelling microorganism *Bacillus thuringiensis* (Bt) as pesticidal agents. These polypeptides have been found to be specifically toxic to particular insects, and microbial formulations have been used commercially for many years as foliarly applied insecticides. It has also recently been found that various forms of the Bt toxin can be toxic to insect pests when expressed inside the tissues of plants on which the insects feed.

Many arthropods express polypeptides capable of killing or incapacitating various pests. Therefore arthropods have been identified as a group of organisms producing polypeptides possessing pesticidal properties. In fact, scorpion venom contains insect-selective toxins affecting ion channels (Zlotkin et al. (1985) *Arch. Biochem. Biophys.* 240:877-87). The toxicity of the different polypeptides operates through multiple pharmacological and biochemical pathways (Zlotkin et al. (1971) *Biochimie* (Paris), 53:1073-1078).

Transgenic dicot plants expressing a toxin obtained from *Androctonus australis* scorpions have been created (U.S. Pat. No. 5,177,308). The AaIT expressing plants have been cross-bred to transgenic plants carrying Bt δ-endotoxin yielding plants with two independent insect-specific toxin traits (U.S. Pat. No. 5,177,308).

Insects predominate as rice pests throughout Asia and are most serious in tropical regions where over 60 species are pests. The most serious rice insect pests are commonly categorized as Homoptera (sucking pests such as leafhoppers and planthoppers) and Lepidoptera (stem borers and defoliators).

The identification of new pesticidal polypeptides is desirable for use in pest-management strategies. It is of particular importance to identify pesticidal toxins that are active against insect pests from the orders Homoptera and Lepidoptera, and against insects that have developed resistance to Bt toxins.

SUMMARY OF THE INVENTION

Compositions and methods for enhancing plant pest resistance, particularly insect pests are provided. Compositions of the invention include isolated polypeptides, peptides, and amino acid sequences and nucleic acid molecules having a nucleotide sequence encoding the polypeptides, peptides, and amino acid sequences of the invention. The polypeptides of the invention were isolated from arthropod venom and telsons and possess pesticidal activity. In an embodiment, the polypeptides of the invention are orally active and affect pests upon ingestion. The invention provides expression cassettes, host cells, baculovirus expression vectors, transformed plant cells, and plants comprising nucleic acid molecules encoding the polypeptides of the invention. In an embodiment, a nucleotide sequence encoding a pesticidal polypeptide of the invention is inserted into the genome of a baculovirus to produce a pesticidal recombinant baculovirus. In this embodiment the presence of the pesticidal polypeptide in the baculovirus increases the efficiency with which the virus acts to kill or incapacitate the pest, thus, enhancing the effectiveness of the baculovirus as an adjunct or replacement for chemical pest control agents.

In an embodiment of the invention, the promoter to which a nucleotide sequence of the invention or a nucleotide sequence encoding a polypeptide of the invention is operably linkedis constitutive, inducible, or tissue-preferred. An embodiment of the invention comprises a vascular tissue preferred promoter operably linked to a nucleotide sequence encoding a polypeptide of the invention. The operably linked promoter is an insect-inducible promoter in one embodiment of the invention.

Methods for altering the pest resistance of a plant are provided. The plant's resistance to pests such as, but not limited to, insects and the pathogens transmitted by insects, may be altered by the methods of the invention. A method of the invention comprises stably transforming into a plant cell a nucleic acid molecule encoding a polypeptide of the invention. The nucleic acid molecule is operably linked to a promoter capable of driving transcription in the plant cell. The transformed plant cell is used to generate a transformed plant. The transformed plant cell and transformed plant are capable of expressing a polypeptide of the invention in the plant cell or plant cells. The polypeptide of the invention possesses pesticidal activity. In an embodiment the pesticidal activity of the polypeptide of the invention is orally active upon ingestion by an insect such as, but not limited to, an insect of the Homopteran, Lepidopteran, and Hymenopteran orders. In an embodiment, the insect infected by the pesticidal activity of the invention exhibits resistance to a Bt toxin.

Methods for identifying polypeptides possessing oral pesticidal activity are provided. In an embodiment, polypeptides are isolated from arthropod venom. The venom is obtained from isolated venom glands. The isolated venom glands have been surgically removed from the organism. In another embodiment, the venom is obtained by harvesting venom from the organism through a process such as, but not limited to, milking the organism. The polypeptides are combined with at least one nutrient to generate a polypeptide solution.

The polypeptide solution is fed to insects. Insecticidal activity is assayed. Insecticidal activity includes, but is not limited to, mortality, weight loss, attraction, and repellency.

Some pesticidal polypeptides modulate sodium channels and are sodium channel neurotoxins. In another embodiment of the invention, nucleic acid sequences encoding potential sodium channel neurotoxins are identified from amino acid and nucleotide sequence data derived from a cDNA library of arthropod telsons. The open reading frames encoding potential sodium channels neurotoxins are amplified from the cDNA and cloned into appropriate expression cassettes. The potentially pesticidal amino acids are tested for oral pesticidal activity.

Compositions of the invention provide antibodies that selectively bind to a polypeptide of the invention.

DETAILED DESCRIPTION OF THE INVENTION

Figure 1:
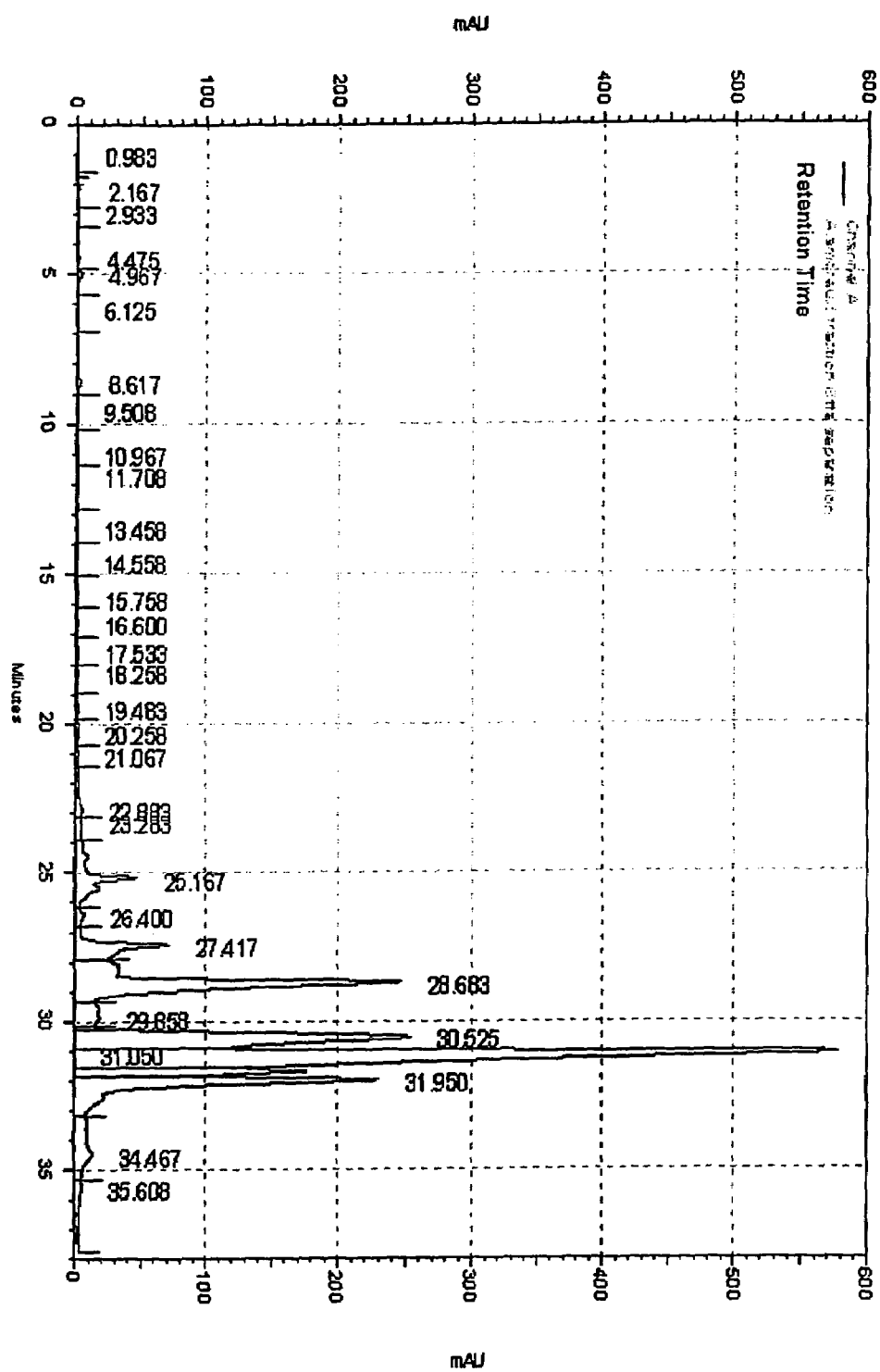
FIG. 1 presents a chromatogram of the purification of Aam1 (SEQ ID NO:20) from a fraction of crude *Androctonus amoreuxi* venom enriched for pesticidal activity. The enriched fraction was loaded onto a Microbore LC C4 column, and the column was developed with an acetonitrile gradient according to Method 5 as described elsewhere herein. The fraction enriched for pesticidal activity was further purified.
Figure 2:
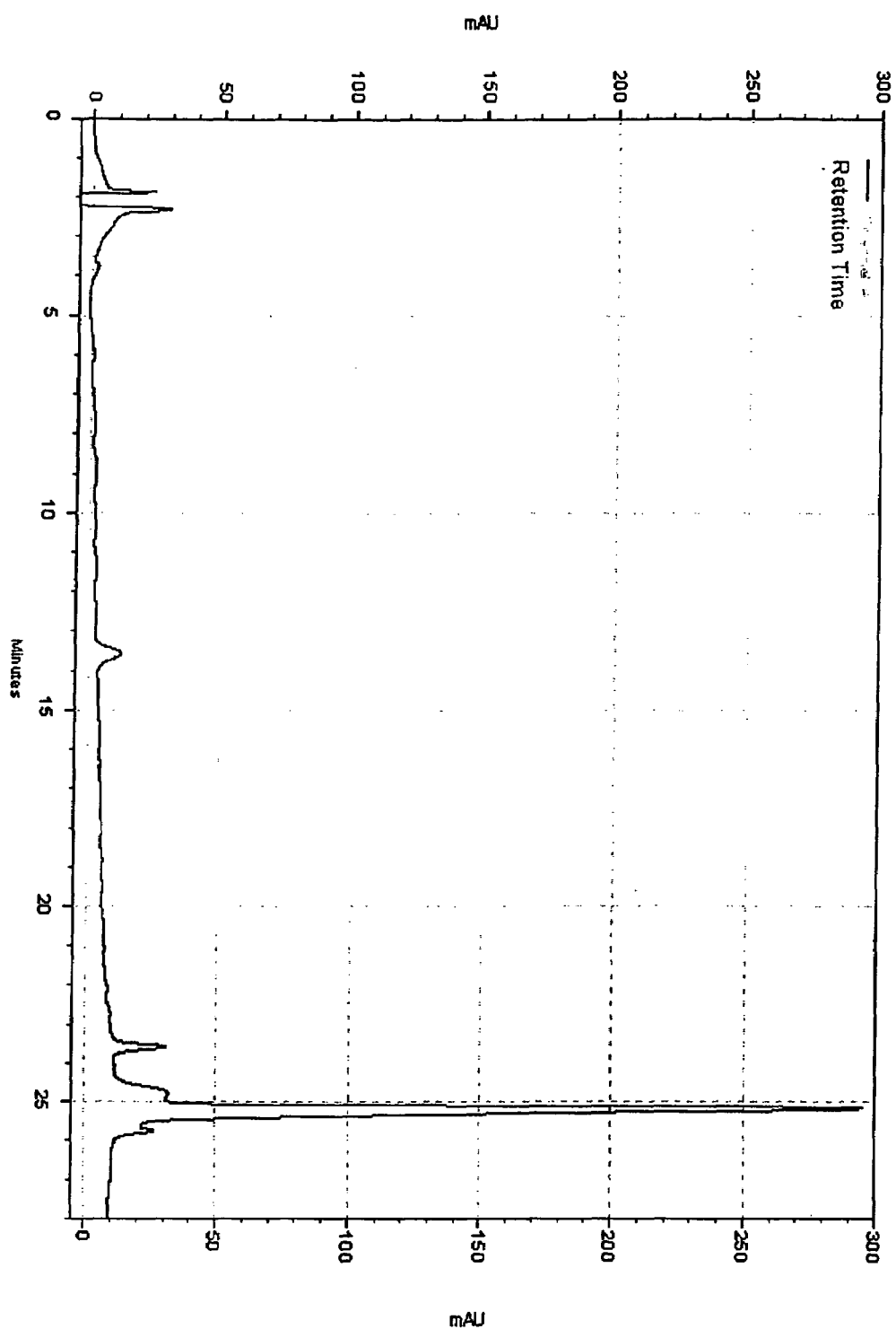
FIG. 2 presents a chromatogram of the further purification of Aam1 (SEQ ID NO:20) from a Microbore LC fraction (see FIG. 1). The enriched fraction was loaded onto a Microbore LC C18 column, and the column was developed with an acetonitrile gradient according to Method 9 as described elsewhere herein.
Figure 3:
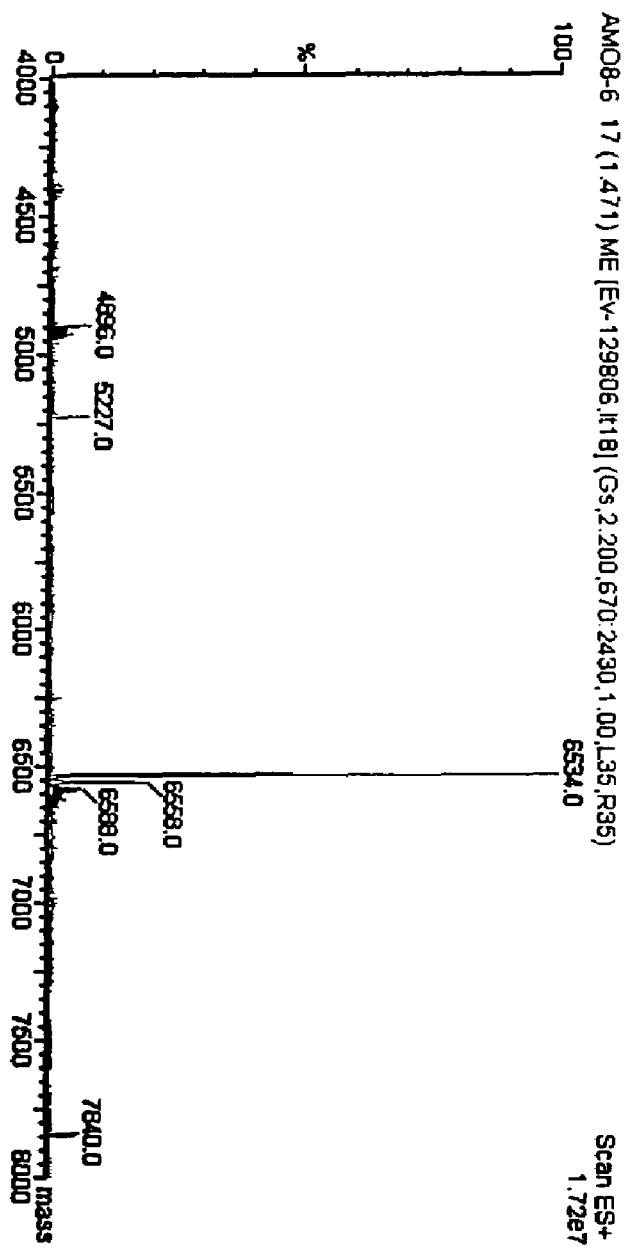
FIG. 3 depicts the results of mass spectroscopy analysis of Aam1 (SEQ ID NO:20).
Figure 4:
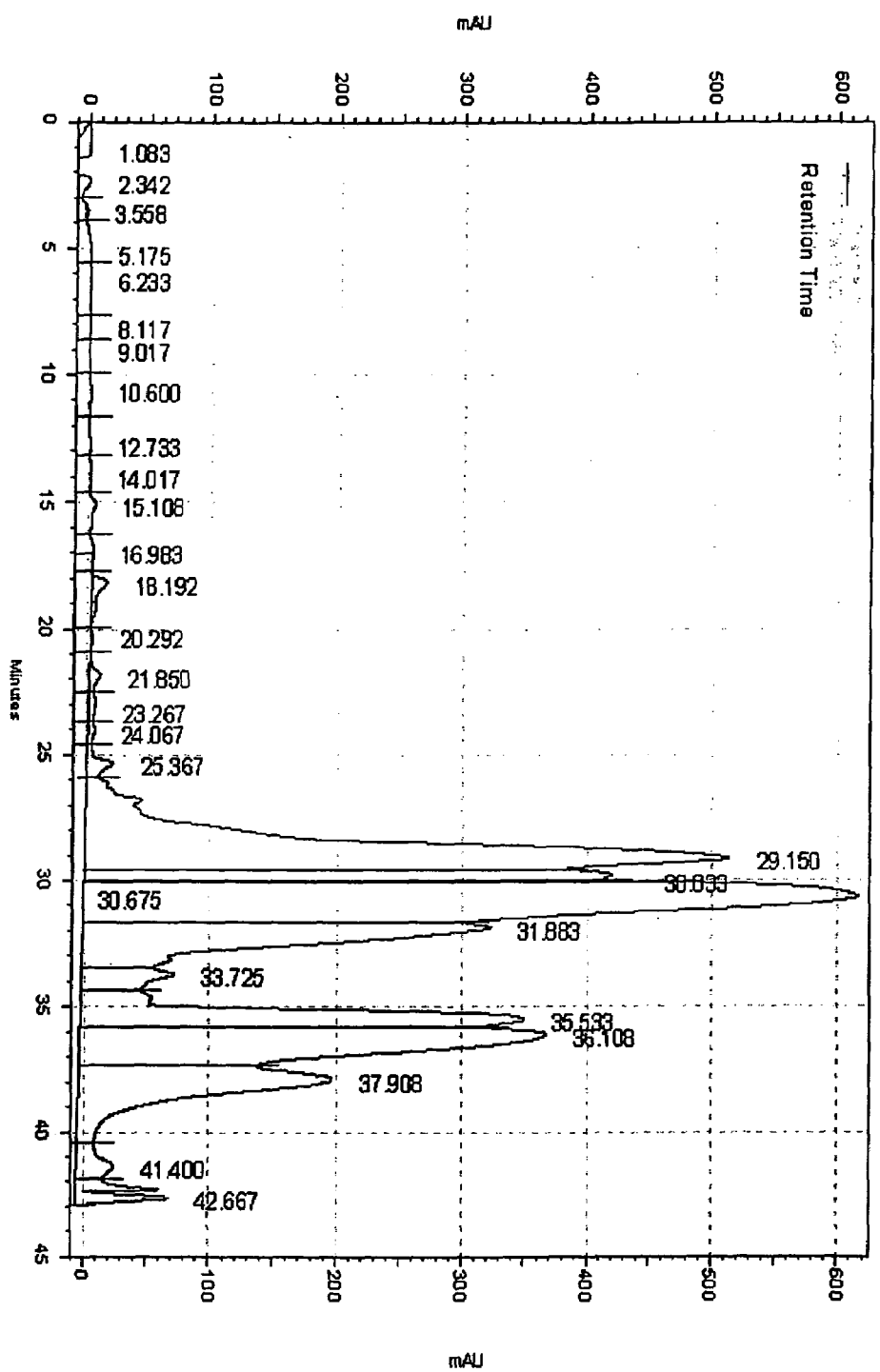
FIG. 4 presents a chromatogram of the purification of Aam2 (SEQ ID NO:27) from a fraction of crude Androctonus amoreuxi venom enriched for pesticidal activity. The enriched fraction was loaded onto a Microbore LC C4 column, and the column was developed with an acetonitrile gradient according to Method 5 as described elsewhere herein. The fraction enriched for pesticidal activity was further purified.
Figure 5:
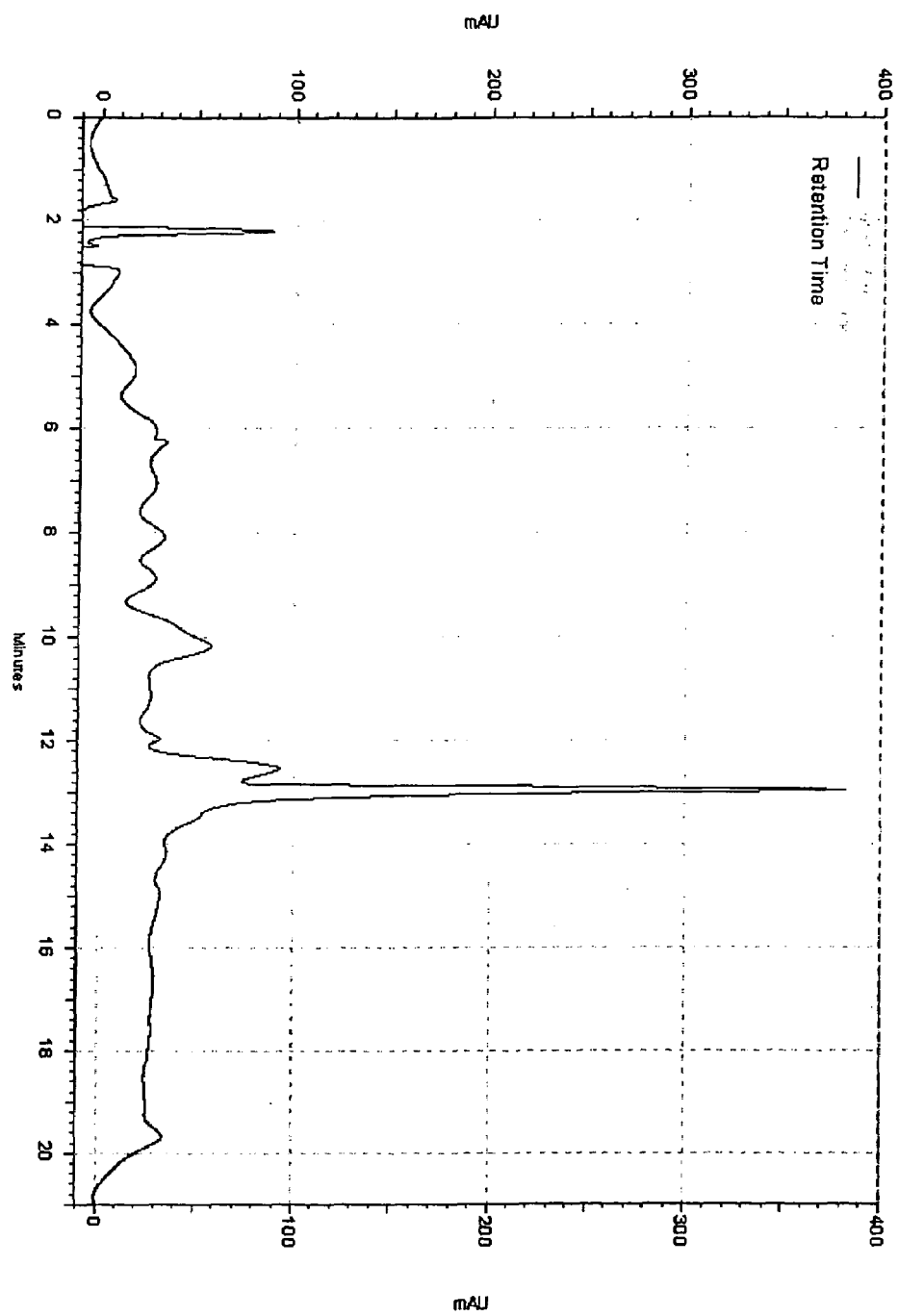
FIG. 5 presents a chromatogram of the further purification of Aam2 (SEQ ID NO:27) from a Microbore LC fraction (see FIG. 4). The enriched fraction was loaded onto a Microbore LC C18 column, and the column was developed with an acetonitrile gradient according to Method 6 as described elsewhere herein.
Figure 6:
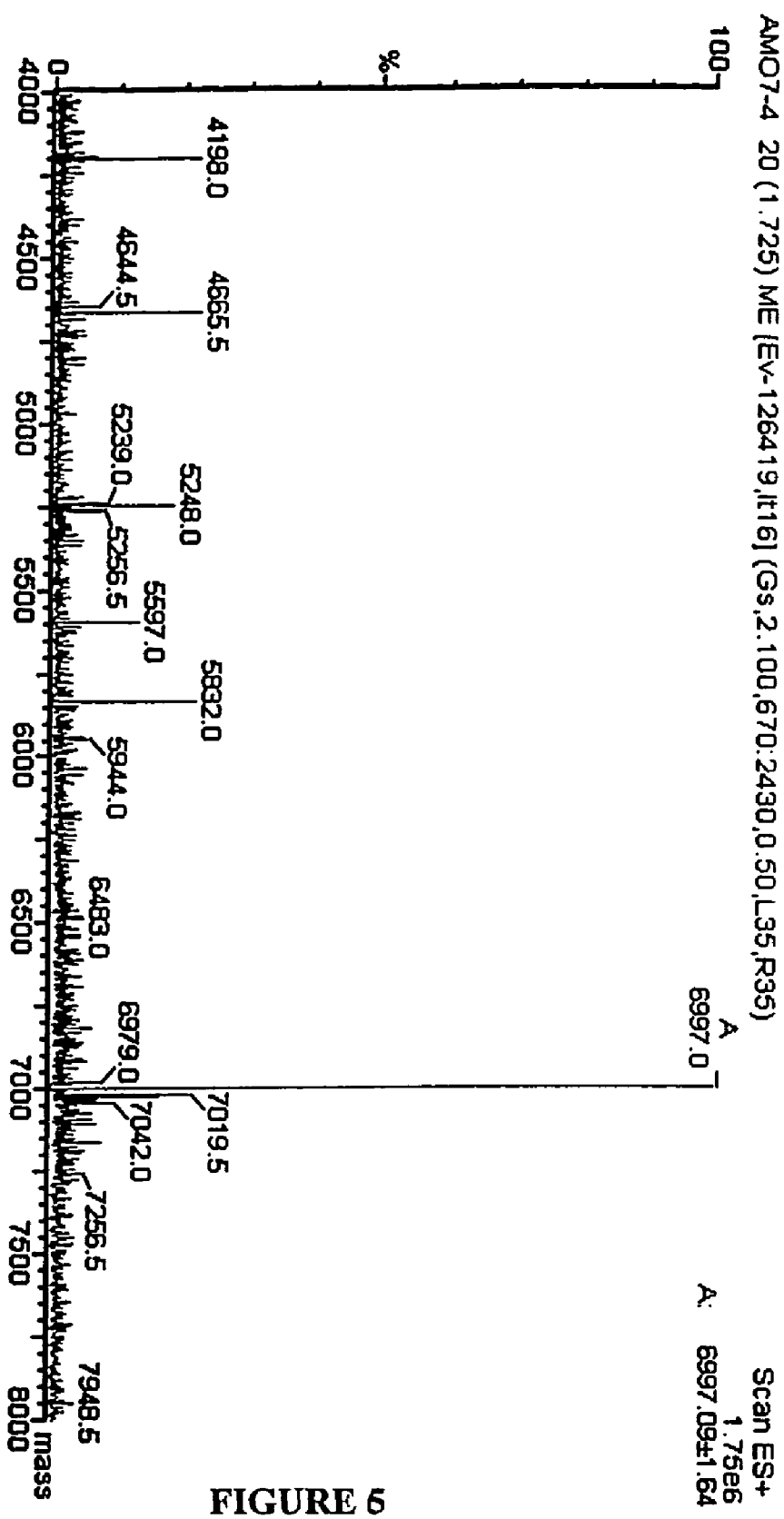
FIG. 6 depicts the results of mass spectroscopy analysis of Aam2 (SEQ ID NO:27).
Figure 7:
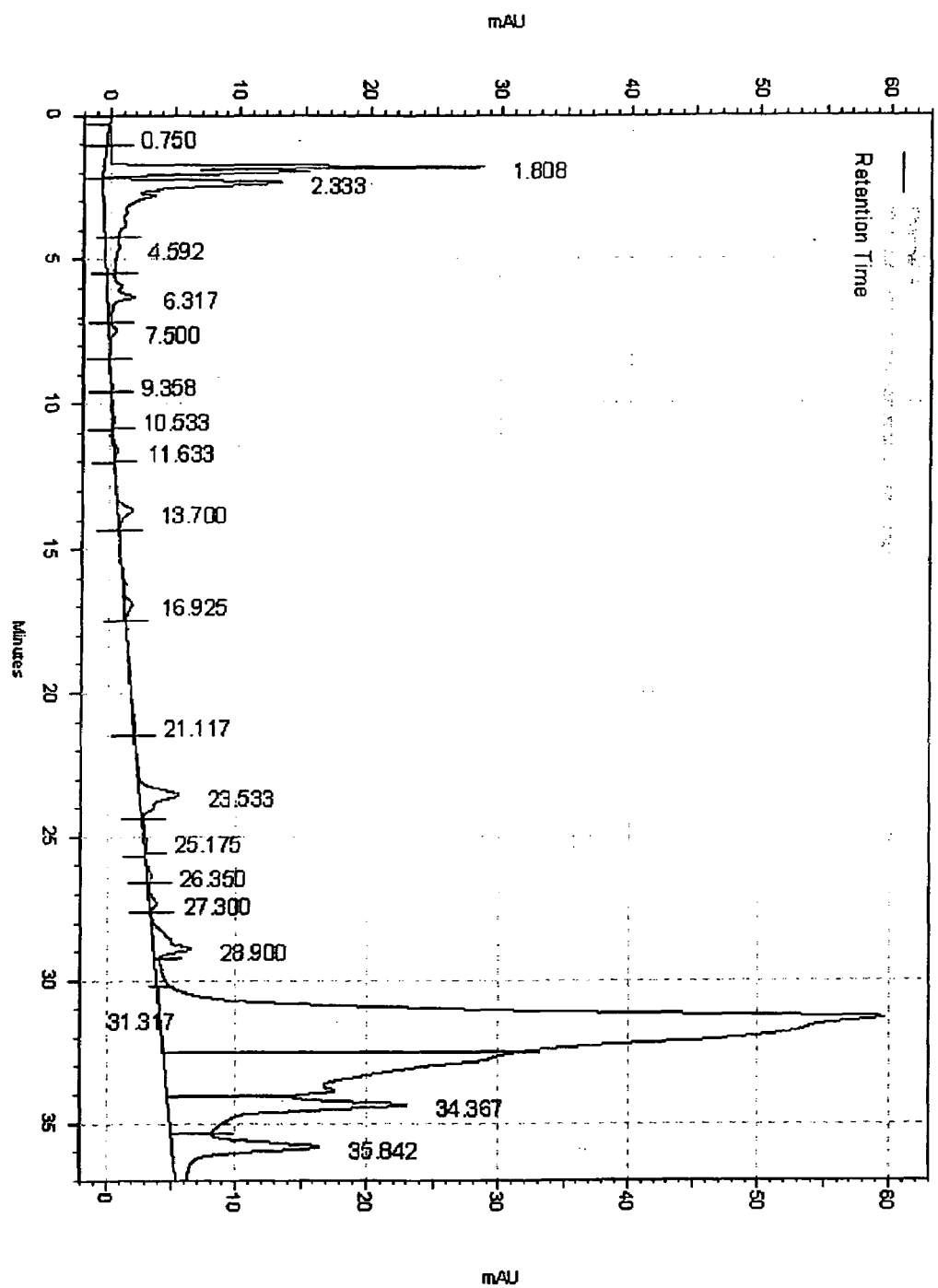
FIG. 7 presents a chromatogram of the purification of CV1 (SEQ ID NO:2 and 4) from a fraction of crude *Centruroides vittatus* venom enriched for pesticidal activity. The enriched fraction was loaded onto a Microbore LC C18 column, and the column was developed with an acetonitrile gradient according to Method 8 as described elsewhere herein.
Figure 8:
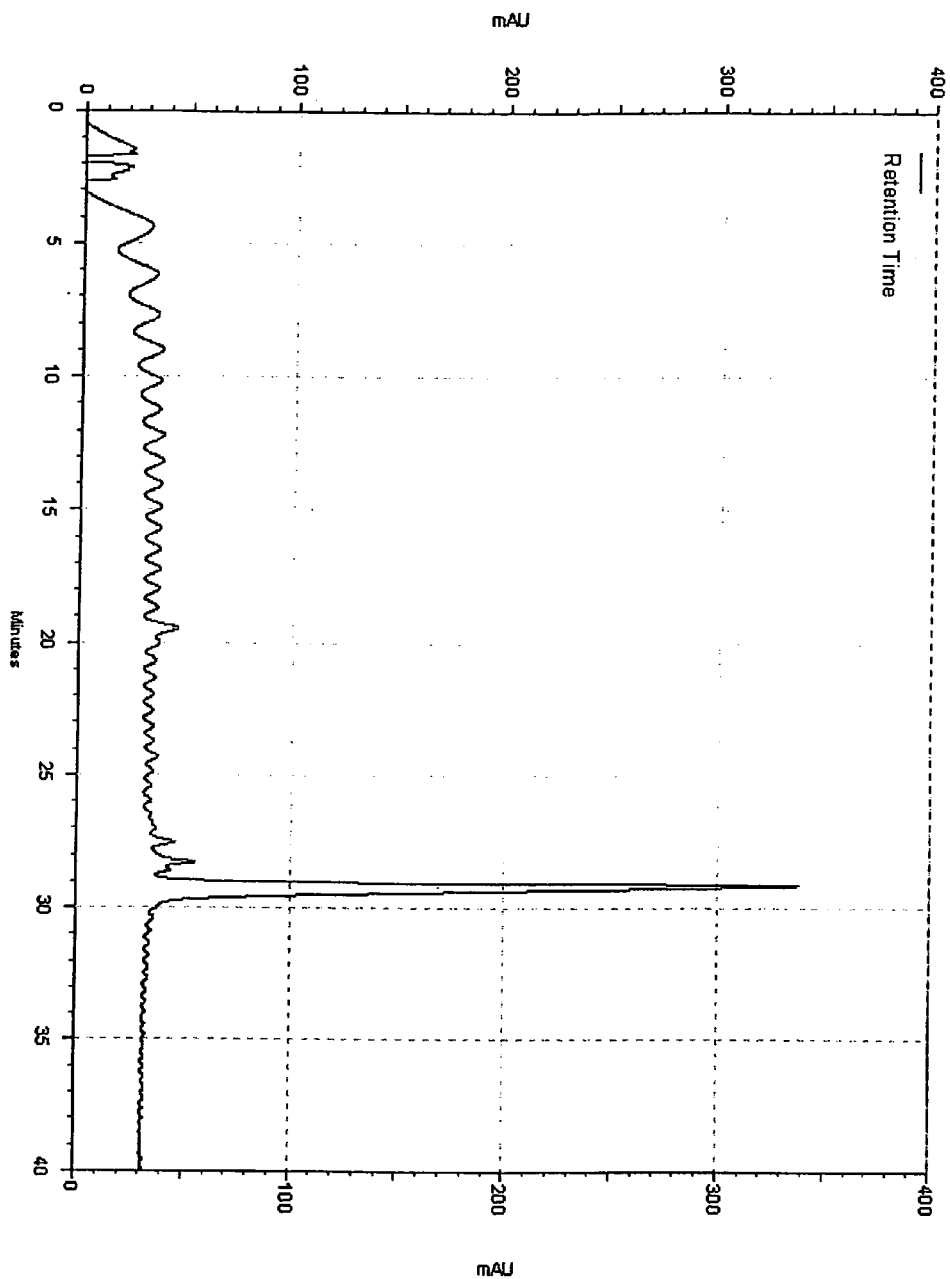
FIG. 8 presents a chromatogram of the purification of LqhIV (SEQ ID NO:7) from a fraction of crude venom enriched for pesticidal activity. The enriched fraction was loaded onto a Microbore LC C18 column, and the column was developed with an acetonitrile gradient according to Method 6 as described elsewhere herein.
Figure 9:
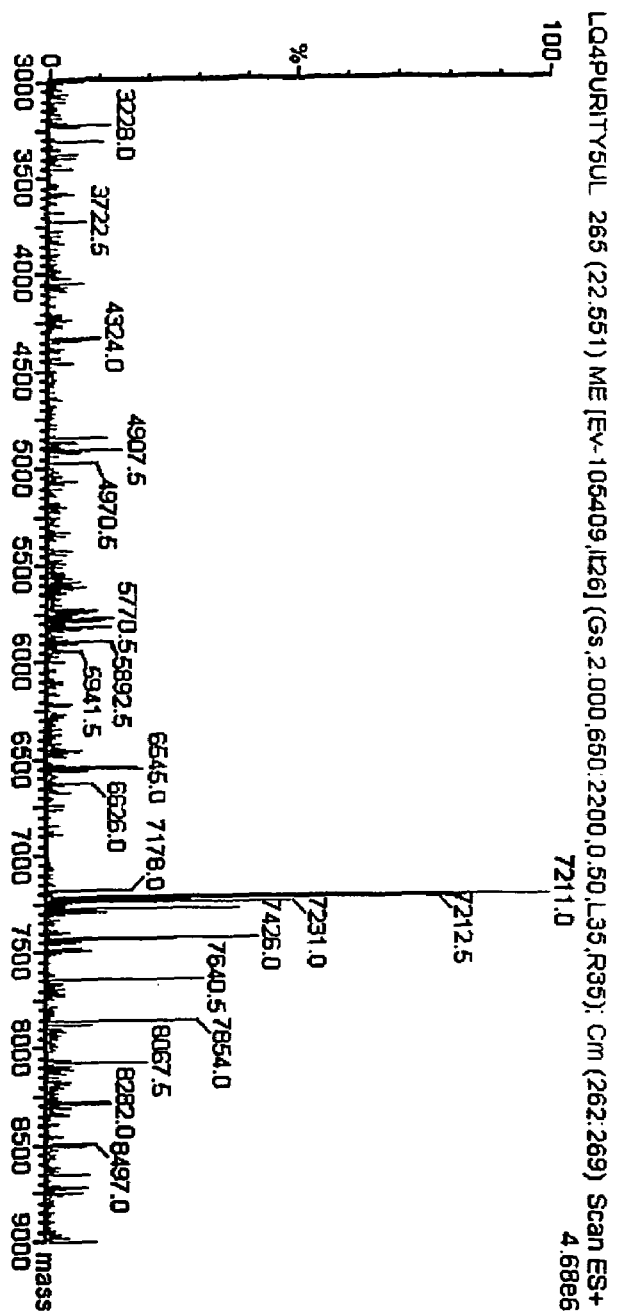
FIG. 9 depicts the results of mass spectroscopy analysis of LqhIV (SEQ ID NO:7).
Figure 10:
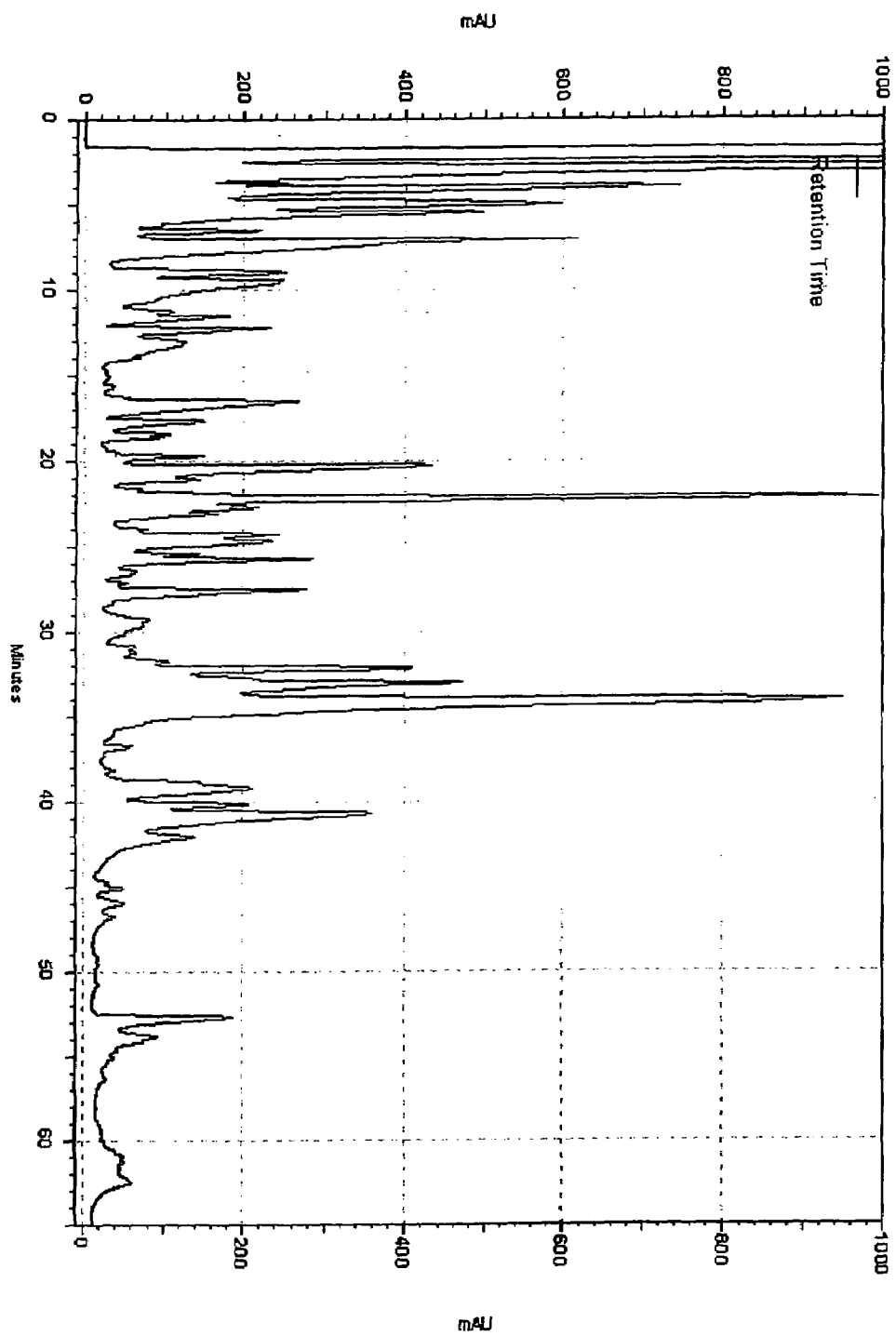
FIG. 10 presents a chromatogram of the purification of VC1 (SEQ ID NO:10) from a fraction of crude *Vaejovis carolinanus* venom enriched for pesticidal activity. The enriched fraction was loaded onto a Microbore LC C4 column, and the column was developed with an acetonitrile gradient according to Method 4 as described elsewhere herein. The fraction enriched for pesticidal activity was further purified.
Figure 11:
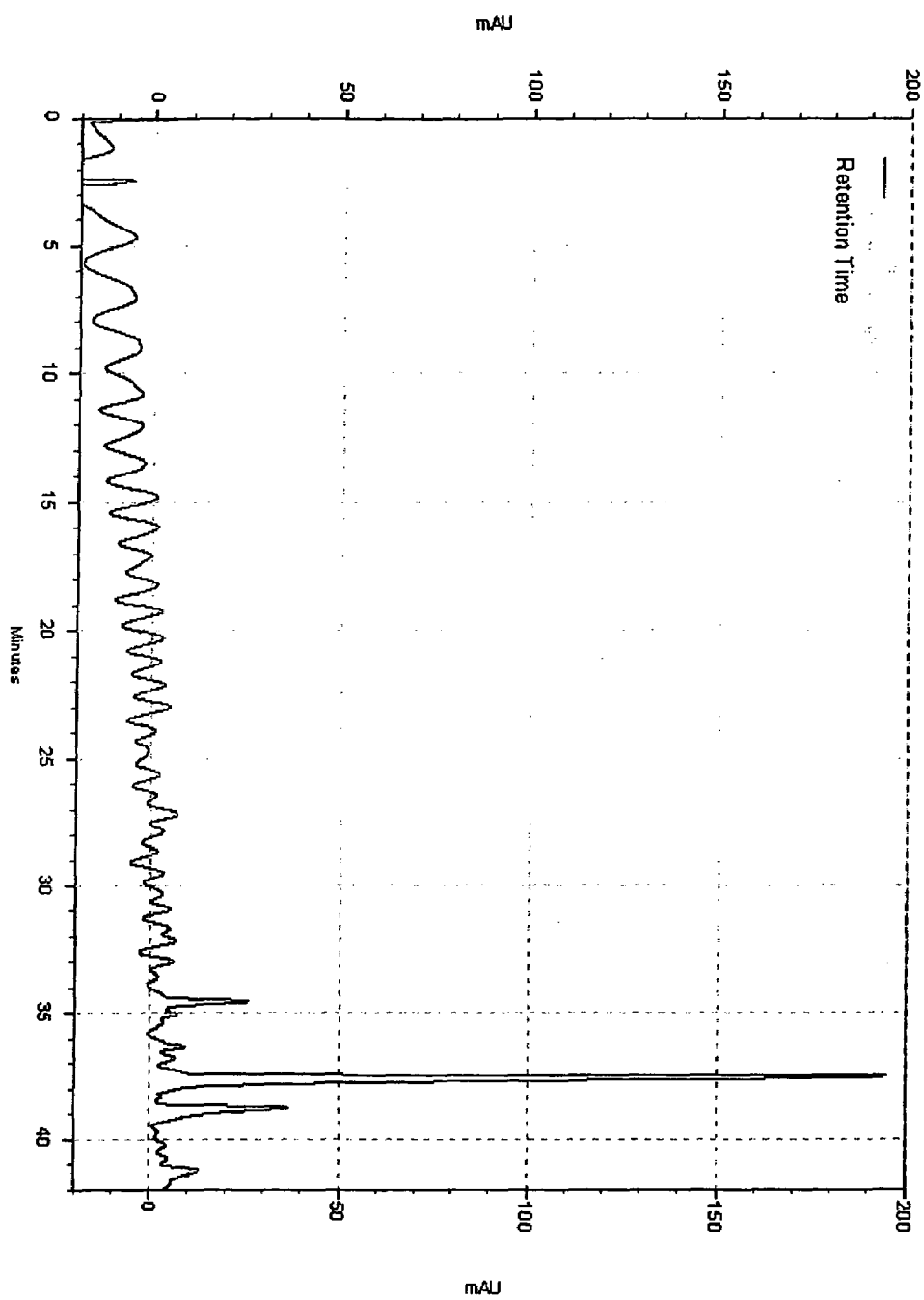
FIG. 11 presents a chromatogram of the further purification of VC1 (SEQ ID NO:10) from a Microbore LC fraction (see FIG. 10). The enriched fraction was loaded onto a Microbore LC C18 column, and the column was developed with an acetonitrile gradient according to Method 6 as described elsewhere herein.
Figure 12:
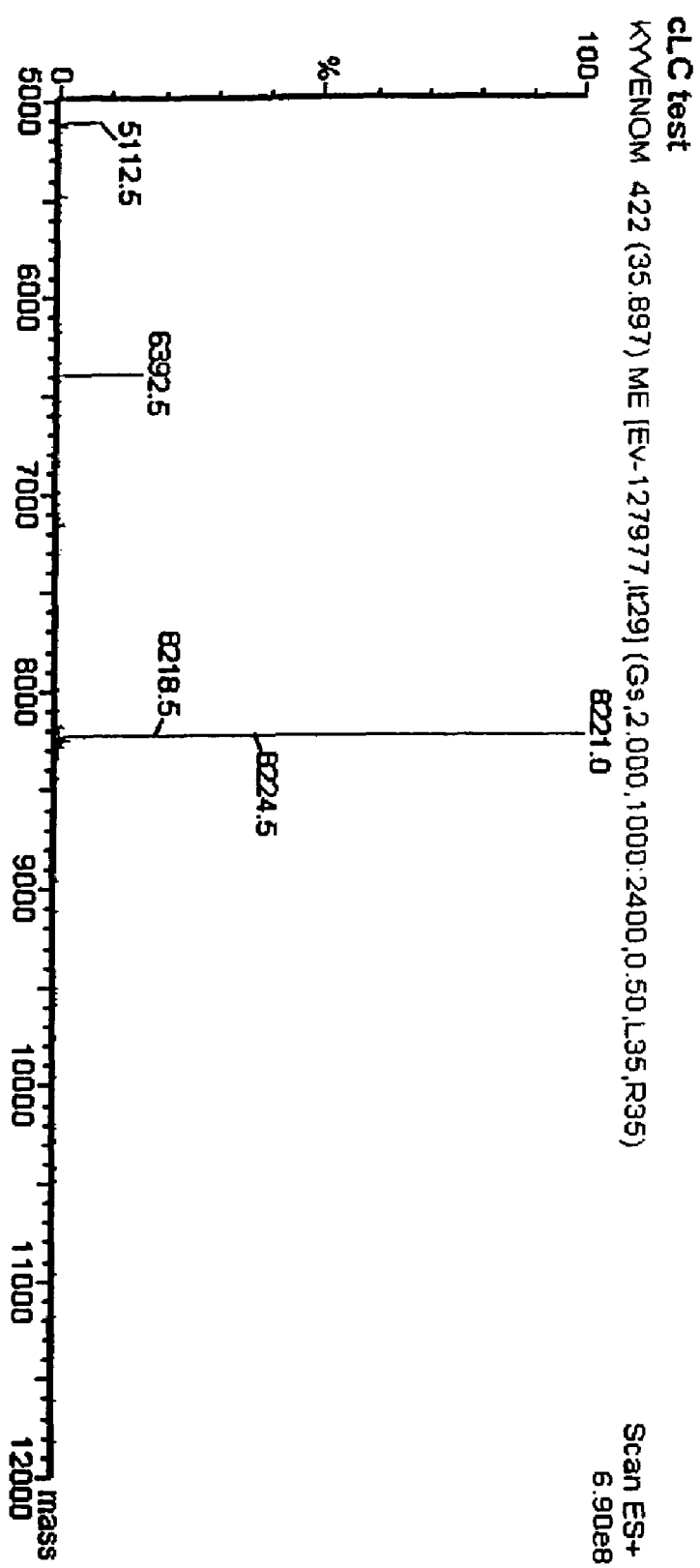
FIG. 12 depicts the results of mass spectroscopy analysis of VC1 (SEQ ID NO:10).
Figure 13:
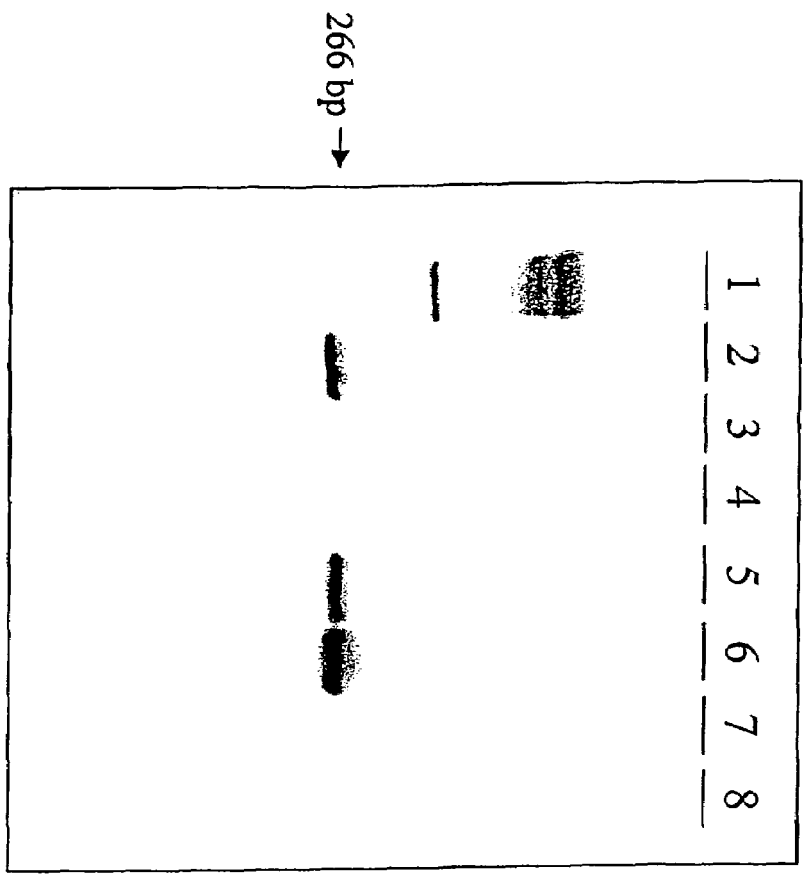
FIG. 13 depicts the results of RT-PCR analysis of transgenic rice plants expressing SP-Aam1 (SEQ ID NOS:15 and 16). Lane 1 contains 100 bp size markers. Lane 2 contains a sample from a vector alone control. Lane 3 contains a sample from a no vector control. Lane 4 contains a sample from wild-type rice. Lanes 5 and 6 contain samples from 2 different transformants, while lanes 7 and 8 contain purified mRNA from the 2 transformants, respectively.

Compositions and methods for impacting pests, particularly insect pests are provided. The polypeptides of the invention were identified in the venom of various arthropods and possess pesticidal properties. These polypeptides are orally active and are toxic to pests upon ingestion by an insect such as, but not limited to, an insect of the Homopteran, Lepidopteran, and Hymenopteran orders. Insect pests of particular importance are those of the Homopteran and Lepidopteran orders. Compositions of the invention include polypeptides and nucleic acid molecules encoding the polypeptides of the invention, expression cassettes comprising the nucleic acid molecules, transformed microorganisms comprising the nucleic acid molecules, vector sequences and host cells for the expression of such polypeptides, and antibodies to the polypeptides. The compositions of the invention further provide plants, and seed thereof, transformed with the nucleic acid molecules of the invention. The transgenic plants of the present invention impact control of Bt toxin-resistant insect species.

The methods of the present invention include methods for altering plant resistance to pests, including insects. Methods for identifying and screening arthropod venom peptides and polypeptides for pesticidal activity are also provided. The methods include HPLC assays directed to the separation and purification of polypeptide toxins, and small-scale, high throughput bioassays to measure the oral pesticidal activity of polypeptides against various species of plant pests.

Compositions of the invention include polypeptides and nucleotide sequences that are involved in altering plant pest resistance. In particular, the present invention provides for isolated nucleic acid molecules comprising nucleotide sequences encoding the amino acid sequences shown in SEQ ID NOS:2, 4, 7, 10, 20, 22, 24, or 27. Further provided are polypeptides having an amino acid sequence encoded by a nucleic acid molecule described herein, for example those set forth in SEQ ID NOS:1, 3, 6, 8, 9, 11, 21, or 23.

"Impacting insect pests" refers to effecting changes in insect feeding, growth and/or behavior, at any stage of development, including, but not limited to, killing the insect, retarding growth, and preventing reproductive capability.

"Pesticidal property" or "pesticidal activity" are used interchangeably herein and are defined as a property or activity of an organism or a substance, such as, for example, a polypeptide, that results in, but is not limited to, pest mortality, pest weight loss, pest attraction, pest repellency, and other behavioral and physical changes of a pest. "Pesticidal polypeptides," "pesticidal peptides," or "pesticidal proteins" are polypeptides, peptides or proteins that display pesticidal activity alone or in combination with other polypeptides. Similarly, an "insecticidal property" or "insecticidal activity" may be used to refer to a "pesticidial activity" when the pest is an insect pest.

"Pesticidally effective amount" is intended as a quantity of a substance or organism having pesticidal properties when present in the environment of a pest. For each substance or organism, the pesticidally effective amount is determined empirically for each pest affected in a specific environment. Similarly an "insecticidally effective amount" may be used to refer to a "pesticidally effective amount" when the pest is an insect pest.

By "orally active" it is intended that the polypeptide retains activity after ingestion of the polypeptide. The orally active polypeptides of the invention are not fully degraded by the digestive system and retain activity after ingestion. After ingestion an orally active polypeptide may be transferred from any component of the digestive system including, but not limited to, the foregut, midgut, hindgut, esophagus, salivary glands, crop, proventriculus, gastric cecae, pyloric valve, Malpighian tubules, ileum, colon, cuticle, nasal passages, pharynx, stomach, small intestine, and large intestine. The polypeptide of the invention may impact cells in any system including, but not limited to, the nervous system, the circulatory system, the digestive system, the musculoskeletal system, the reproductive system, and the excretory system. Insect digestive systems degrade and inactivate most peptides and polypeptides that enter it; the polypeptides of the invention are not inactivated during digestion. The orally active polypeptide may enter an insect target's hemolymph from the digestive system. The orally active polypeptide may enter a mammal's blood from the digestive system.

By "test unit" any structure or container is intended that could contain a solution of the polypeptide to be screened and insects. Such containers are known to one of skill in the art including, but not limited to, 96 well plates, petri plates, 384 well plates, thermocycling plates, microplates, 8 well plates, 12 well plates, microfuge tubes, multi-well tissue culture plates, thermocycling tubes, multiwell assay plates, ELISA plates, petri dishes, dialysis tubing, polystyrene tubing, plastic tubing, and microtiter plates.

By "membrane solution" a composition is intended that is capable of forming a barrier on which an insect can stand and through which the insect can feed. One of skill in the art will recognize that multiple formulations of membrane solutions are available including, but not limited to, 1% Fluoropolymer in PF 5080 solvent.

By "cold-immobilized" exposure to low temperatures is intended that is sufficient to slow the metabolism of an organism but not permanently damage the organism. One of skill in the art will recognize that the conditions that result in cold-immobilization vary depending on the organism in question; such conditions include, but are not limited to, incubating the organism on ice for 1 to 2 minutes.

By "disrupting" stimulation is intended by such means as forceful movement, rapid movement, repeated movement, or incubation at elevated temperatures. One of skill in the art will recognize that disrupting may be accomplished by a variety of methods, including but not limited to, tapping, shaking, rocking, or warming the test unit at 42° C. for 1 to 3 minutes.

The present invention provides new approaches for impacting pests that do not depend on the use of traditional chemical insecticides. The invention involves the isolation of polypeptides and the genes that encode them. Such polypeptides comprise pesticidal polypeptides with pesticidal activity against pests, particularly insect pests of the Homopteran, Lepidopteran and Hymenopteran orders, and more particularly insect pests of the Homopteran and Lepidopteran orders. The pesticidal polypeptides of the invention are isolated from the venom of arthropods such as spiders, scorpions, centipedes and wasps; predators that rely on insecticidal chemicals likely to have unique toxicity to insects.

It has been demonstrated, notably with the toxins produced by the soil dwelling microorganism *Bacillus thuringiensis*, that pesticidal toxins can successfully be produced in plant cells so as to render the transgenic plants toxic to pests that ingest them. The *Bacillus thuringiensis* pesticidal toxins are selectively toxic to insect pests and do not demonstrate toxicity to mammals. The present invention is directed to pesticidal polypeptides that are toxic to plant pests. In one embodiment, the peptides of the present invention are not toxic to livestock or humans upon consumption of plants expressing the claimed peptide or polypeptide. In another embodiment, the peptides of the invention are expressed in plants not intended for consumption by livestock or humans, wherein mammalian toxicity is not an issue.

The invention provides compositions and methods for producing transgenic plants that express the pesticidal polypeptides of the invention, transgenic microorganisms that express the pesticidal polypeptides of the invention, and pesticidal polypeptide compositions that enhance the resistance of plants to pests, particularly insect pests of the Homopteran, Lepidopteran and Hymenopteran orders, and more particularly insect pests of the Homopteran and Lepidopteran orders.

One embodiment of the invention provides transgenic rice plants that express one or more pesticidal polypeptides of the invention and possess enhanced resistance to insects. The polypeptides of the invention exhibit pesticidal activity against insects including, but not limited to, Homopteran, Lepidopteran and Hymenopteran species. Insects of particular interest include the green leafhopper, *Nephotettix virescens*; the brown planthopper, *Nilaparvata lugens*; and *Scirpophaga incertulas*. In an embodiment of the invention, transgenic rice plants control insects that vector viruses causing diseases such as rice tungro and rice stunt, thereby, significantly curtailing virus epizootics and adding substantially to plant vigor and rice yield. An embodiment of the invention is transgenic plants such as, but not limited to, rice, that exhibit multiple pesticidal activities. The multiple pesticidal activities result from expression of one or more of the polypeptides of the invention in the transgenic plant. In an embodiment, the transgenic plants possess resistance to multiple species of insects. The polypeptides of the invention expressed by the transgenic plant inhibit insect activity through one or more pathways. The multiplicity of pesticidal activities exhibited by the transgenic plant decreases the evolution of insects resistant to the polypeptides of the invention. Provided in the invention is a transgenic rice plant possessing resistance to both Homopteran and Lepidopteran species of pests, and retaining resistance to Lepidopteran pests resistant to Bt toxin.

Compositions of the invention include amino acid sequences corresponding to pesticidal toxins isolated from various arthropod venoms. In particular, the present invention provides isolated polypeptides comprising the amino acid sequences shown in SEQ ID NOS:2, 4, 7, 10, 13, 15, 16, 18, 19, 20, 22, 24, 26, and 27, and the nucleotide sequences that encode these polypeptides. Also included in the compositions of the invention are fragments and variants of these polypeptides. Of particular interest are optimized nucleotide sequences encoding the pesticidal polypeptides of the invention. By "optimized nucleotide sequences," sequences are intended that are optimized for expression in a particular organism. Such optimized nucleotide sequences may be prepared for any organism of interest using methods known in the art, described elsewhere herein. SEQ ID NOS:5, 12, and 14 disclose nucleotide sequences operably linked to signal sequences, optimized for expression in rice, and encoding the polypeptides set forth in SEQ ID NOS:4, 13, and 15 and 16. SEQ ID NO:17 discloses a nucleotide sequence operably linked to a BAA signal sequence, optimized for expression in plants, and encoding the polypeptides set forth in SEQ ID NOS:18 and 19. SEQ ID NO:25 discloses a nucleotide sequence operably linked to a BAA signal peptide, optimized for expression in plants, and encoding the polypeptide set forth in SEQ ID NO:26. Nucleotide sequences of the invention can be similarly optimized for expression in any organism. Nucleotide sequences optimized for expression in crop plants such as rice, wheat, corn, soybeans, rye, barley, and alfalfa are of particular interest.

The polypeptides of the invention were isolated from the venom of various species of arthropods. These polypeptides possess pesticidal activity against pests including, but not limited to, the southern corn rootworm and European corn borer.

The polypeptide set forth in SEQ ID NO:2 and SEQ ID NO:4, was isolated from Centruroides vittatus venom and is also known as CV1. Nucleotides 49 to 303 of SEQ ID NO:1 and SEQ ID NO:3 encode CV1. SEQ ID NO:5 is an artificial sequence that encodes BAA-CV1 utilizing codons optimized for expression in Oryza sativa. SEQ ID NO:5 contains a nucleotide sequence encoding the barley alpha amylase (BAA) signal peptide (Rahmatullah, et al. (1989) Plant Mol. Biol. 12:119-121, herein incorporated by reference) operably linked to a nucleotide sequence encoding CV1.

The polypeptide set forth in SEQ ID NO:7 was isolated from Leiurus quinquestriatus venom and is also known as LqhIV. The nucleotide sequence set forth in SEQ ID NO:8 and nucleotides 38 to 289 of SEQ ID NO:6 encode the LqhIV polypeptide.

The polypeptide set forth in SEQ ID NO:10 was isolated from Vaejovis carolinanus venom and is also known as VC1. The nucleotide sequence set forth in SEQ ID NO:11 and nucleotides 65 to 358 of SEQ ID NO:9 encode the VC1 polypeptide. SEQ ID NO:12 is an artificial sequence that encodes PR1-VC1 utilizing codons optimized for expression in Oryza sativa. SEQ ID NO:12 contains a nucleotide sequence encoding the PR1 signal peptide (Cornelissen, et al. (1986) Nature 321:531-532, herein incorporated by reference) operably linked to a nucleotide sequence encoding VC1; the polypeptide encoded by the nucleotide sequence set forth in SEQ ID NO:12 is set forth in SEQ ID NO:13.

The polypeptide set forth in SEQ ID NO:20 was isolated from Androctonus amoreuxi venom and is also known as Aam1. SEQ ID NO:14 is an artificial sequence that encodes SP-Aam1 utilizing codons optimized for expression in Oryza sativa. SEQ ID NO:14 contains a nucleotide sequence encoding the sweet potato sporamin (SP) signal sequence (Hattori, et al (1985) Plant Mol. Biol. 5:313-320, herein incorporated by reference) operably linked to a nucleotide sequence encoding Aam1; the polypeptide encoded by the nucleotide sequence set forth in SEQ ID NO:14 is set forth in SEQ ID NO:15 and SEQ ID NO:16. SEQ ID NO:17 is an artificial sequence that encodes BAA-Aam1 utilizing codons optimized for expression in Streptomyces coelicolor. SEQ ID NO:17 contains a nucleotide sequence encoding the BAA signal peptide operably linked to a nucleotide sequence encoding Aam1; the polypeptide encoded by the nucleotide sequence set forth in SEQ ID NO:17 is set forth in SEQ ID NO:18 and SEQ ID NO:19.

The nucleotide sequence encoding the polypeptide set forth in SEQ ID NO:22 and SEQ ID NO:24 was identified from a Centruroides vittatus telsons cDNA library. SEQ ID NO:23 and nucleotides 117 to 359 of SEQ ID NO:21 encode Ts7, the polypeptide set forth in SEQ ID NO:22 and 24. SEQ ID NO:25 is an artificial sequence that encodes BAA-Ts7 utilizing codons optimized for expression in Streptomyces coelicolor; the polypeptide encoded by the nucleotide sequence set forth in SEQ ID NO:25 is set forth in SEQ ID NO:26. The polypeptide set forth in SEQ ID NO:27 was isolated from Androctonus amoreuxi venom and is also known as Aam2.

The invention discloses isolated polypeptides possessing pesticidal properties and the nucleotide sequences that encode them. These molecules find use in methods for impacting pests, particularly insect pests. The nucleotide sequences of the invention may be used to transform any organism to produce the encoded pesticidal polypeptides. Methods are provided that involve the use of such transformed organisms to impact or control plant pests.

The invention encompasses a plant transformed with at least one nucleotide sequence of the invention. The plant is stably transformed with a nucleotide construct comprising at least one nucleotide sequence of the invention operably linked to a promoter that drives expression in a plant cell. While the invention does not depend on a particular biological mechanism for increasing the resistance of a plant to a plant pest, expression of the nucleotide sequences of the invention in a plant can result in the production of the pesticidal polypeptides of the invention and in an increase in the resistance of the plant to a plant pest. The plants of the invention find use in agriculture in methods for impacting insect pests. Certain embodiments of the invention provide rice plants that find use in methods for impacting both Homopteran and Lepidopteran species of insect pests.

In one such embodiment, ingestion of transgenic rice plant tissue expressing the Aam1 polypeptide by Homoptera and Lepidoptera species of insect results in toxicity to both species of insect pests. Aam1 (SEQ ID NO:20) is an orally active insecticidal polypeptide active against both Homopteran and Lepidopteran species of insect. Furthermore, transgenic rice plant tissue expressing Aam1 is also toxic to insect populations resistant to the Lepidopteran specific δ-endotoxin from Bacillus thuringiensis (Bt). Thus, in an embodiment, the transgenic plants of the present invention protect field crops and facilitate control of Bt toxin-resistant insect species.

In another embodiment of the invention a nucleotide sequence encoding an insecticidal polypeptide of the invention is inserted into the genome of a baculovirus to yield an insecticidal recombinant baculovirus. The recombinant baculovirus expresses the insecticidal polypeptide. The presence of the insecticidal polypeptide in the baculovirus increases the efficiency with which the virus acts to kill or incapacitate the insect, thus enhancing the effectiveness of the baculovirus in pest management techniques. Compositions of the invention include such recombinant baculoviruses.

The invention further encompasses microorganisms transformed with at least one nucleic acid molecule of the invention, with an expression cassette comprising the nucleotide molecule, or with a vector molecule comprising the expression cassette. Microorganisms that multiply on plants are of particular interest.

The invention provides pesticidal compositions. The invention encompasses pesticidal compositions comprising an isolated polypeptide of the invention, alone or in combination with a transformed organism of the invention and a suitable carrier. In an embodiment, the pesticidal composition comprises a transformed organism of the invention. Such a pesticidal composition contains a transformed microorganism at pesticidally effective levels and a suitable carrier.

It is recognized that the pesticidal polypeptides may vary in molecular characteristics and activity against particular pests. However, by the methods set forth herein, polypeptides active against a variety of pests may be isolated and characterized.

The pesticidal polypeptides of the invention can be used in combination with Bt endotoxins or other insecticidal polypeptides to increase insect target range. Furthermore, the use of the pesticidal polypeptides of the present invention in combination with Bt endotoxins or other types of insecticides of a distinct nature has utility in the prevention and/or management of insect resistance. Insecticides include, but are not limited to, protease inhibitors (both serine and cysteine types), lectins, α-amylases, and peroxidases.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 9%, 8%, 7%, 6%, 5%, 4%, 3%, 2%, or 1% (by dry weight) of contaminating protein. When the protein of the invention or biologically active portion thereof is recombinantly produced, preferably culture medium represents less than about 30%, 20%, 10%, 9%, 8%, 7%, 6%, 5%, 4%, 3%, 2%, or 1% (by dry weight) of chemical precursors or non-protein-of-interest chemicals.

Fragments and variants of the disclosed nucleotide sequences and polypeptides encoded thereby are also encompassed by the present invention. By "fragment" a portion of the nucleotide sequence and hence polypeptide encoded thereby, or a portion of the amino acid sequence is intended. Fragments of a nucleotide sequence may encode polypeptide fragments that retain the biological activity of the native polypeptide and hence possess pesticidal activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a nucleotide sequence of the invention that encodes a biologically active portion of a pesticidal polypeptide of the invention will encode at least 10, 15, 20, 25, 30, 35, 40, 45, 50, 55, 60, or 64 contiguous amino acids of SEQ ID NOS:2 and 4; at least 10, 15, 20, 25, 30, 35, 40, 45, 50, 55, 60, 65, 70, 75, 80, 85, or 87 contiguous amino acids of SEQ ID NO:7; at least 10, 15, 20, 25, 30, 35, 40, 45, 50, 55, 60, 65, 70, 75, 80, 85, 90, 95, or 97 contiguous amino acids of SEQ ID NO:10; at least 10, 15, 20, 25, 30, 35, 40, 45, 50, 55, or 58 contiguous amino acids of SEQ ID NO:20; at least 10, 15, 20, 25, 30, 35, 40, 45, 50, 55, or 57 contiguous amino acids of SEQ ID NOS:22 and 24; and at least 10, 15, 20, 25, 30, 35, 40, 45, 50, 55, 60, or 64 contiguous amino acids of SEQ ID NO:27 or up to the total number of amino acids present in a polypeptide of the invention. Fragments of a nucleotide sequence of the invention that are useful as hybridization probes or PCR primers generally need not encode a biologically active portion of a polypeptide of the invention.

Thus, a fragment of a nucleotide sequence of the invention may encode a biologically active portion of a pesticidal polypeptide, or it may be a fragment that can be used as a hybridization probe or PCR primer using methods disclosed below. A biologically active portion of a pesticidal polypeptide can be prepared by isolating a portion of one of the nucleotide sequences of the invention, expressing the encoded portion of the pesticidal polypeptide (e.g., by recombinant expression in vitro), and assessing the activity of the encoded portion of the pesticidal polypeptide. Nucleic acid molecules that are fragments of a nucleotide sequence of the invention comprise at least 15, 20, 30, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 355, or up to the number of nucleotides present in SEQ ID NO:1; at least 15, 20, 30, 40, 50, 60, 70, 75, 80, 90, 100, 110, 120, 125, 130, 140, 150, 160, 170, 175, 180, 190, 200, 210, 220, 230, 240, 250, 254, or up to the number of nucleotides present in SEQ ID NO:3; at least 15, 20, 30, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 355, 360, 365, 370, 375, or up to the number of nucleotides present in SEQ ID NO:6; at least 15, 20, 30, 40, 50, 60, 70, 75, 80, 90, 100, 110, 120, 125, 130, 140, 150, 160, 170, 175, 180, 190, 200, 210, 220, 230, 240, 250, 260, 261, or up to the number of nucleotides present in SEQ ID NO:8; at least 15, 20, 30, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 355, 360, 365, 370, 375, 380, 385, 390, 395, 400, 410, 420, 430, 440, 450, 460, 470, 480, 483, or up to the number of nucleotides present in SEQ ID NO:9; at least 15, 20, 30, 40, 50, 60, 70, 75, 80, 90, 100, 110, 120, 125, 130, 140, 150, 160, 170, 175, 180, 190, 200, 210, 220, 230, 240, 250, 260, 270, 280, 290, 294, or up to the number of nucleotides present in SEQ ID NO:11; at least 15, 20, 30, 40, 50, 60, 70, 75, 80, 90, 100, 110, 120, 125, 130, 140, 150, 160, 170, 175, or 177 nucleotides encoding a portion of the amino acid sequence set forth in SEQ ID NO:20; at least 15, 20, 30, 40, 50, 60, 70, 75, 80, 90, 100, 110, 120, 125, 130, 140, 150, 160, 170, 175, 180, 190, 200, 210, 220, 230, 240, 250, 260, 270, 280, 290, 300, 310, 320, 330, 340, 350, 355, 360, 365, 370, 375, 380, 385, 390, 395, 400, 410, 420, 430, 440, 450, 460, 470, 479, or up to the number of nucleotides present in SEQ ID NO:21; at least 15, 20, 30, 40, 50, 60, 70, 75, 80, 90, 100, 110, 120, 125, 130, 140, 150, 160, 170, 175, 180, 190, 200, 210, 220, 230, 240, 243, or up to the number of nucleotides present in SEQ ID NO:23; and at least 15, 20, 30, 40, 50, 60, 70, 75, 80, 90, 100, 110, 120, 125, 130, 140, 150, 160, 170, 175, 180, 185, 190, or 195 nucleotides encoding a portion of the amino acid sequence set forth in SEQ ID NO:27.

By "variants" substantially similar sequences are intended. For nucleotide sequences, conservative variants include those sequences that, because of the degeneracy of the genetic code, encode the amino acid sequence of one of the pesticidal polypeptides of the invention. Naturally occurring allelic variants such as these can be identified with the use of well-known molecular biology techniques, such as, for example, polymerase chain reaction (PCR) and hybridization techniques as outlined below. Variant nucleotide sequences also include synthetically derived nucleotide sequences, such as those generated, for example, by using site-directed mutagenesis but which still encode a pesticidal polypeptide of the invention. Generally, variants of a particular nucleotide sequence of the invention will have at least about 40%, 45%, 50%, 55%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters. Thus, isolated sequences that encode a pesticidal polypeptide and which hybridize under stringent conditions to the sequences disclosed herein, or to fragments thereof, are encompassed by the present invention.

Variants of a particular nucleotide sequence of the invention (i.e., the reference nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptides of the invention (for example, SEQ ID NO: 2, 4, 7, 10, 20, 22, 24, or 27) are disclosed. Percent sequence identity between any two polypeptides can be calculated using sequence alignment programs described elsewhere herein using default parameters. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity.

By "variant protein" a protein is intended that is derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Variant proteins encompassed by the present invention are biologically active, that is they continue to possess the desired biological activity of the native polypeptide, that is, pesticidal activity as described herein. Such variants may result from, for example, genetic polymorphism or from human manipulation. Biologically active variants of a native pesticidal protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the pesticidal polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Polypeptide Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired pesticidal activity. Obviously, the mutations that will be made in the DNA encoding the variant must not place the sequence out of reading frame and preferably will not create complementary regions that could produce secondary mRNA structure. See EP Patent Application Publication No. 75,444, herein incorporated by reference.

The deletions, insertions, and substitutions of the polypeptide sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays such as, but not limited to, insect feeding assays. See, for example, Marrone et al. (1985) *J. Econ. Entomol.* 78:290-293 and Czapla and Lang (1990) *J. Econ. Entomol.* 83:2480-2485, herein incorporated by reference, or also in Example 2, herein.

Variant nucleotide sequences and proteins also encompass sequences and proteins derived from a mutagenic and recombinogenic procedure such as DNA shuffling. With such a procedure, one or more different orally active pesticidal coding sequences can be manipulated to create new orally active pesticidal polypeptides possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest or any fragment of a nucleotide sequence of the invention may be shuffled between a nucleotide sequence of the invention and corresponding portions of other known pesticides to obtain a new gene coding for a polypeptide with an improved property of interest. Properties of interest include, but are not limited to, pesticidal activity per unit of pesticidal polypeptide, polypeptide stability, toxicity to non-target species particularly humans, livestock, plants, baculovirus and other organisms that express the pesticidal polypeptide of the invention, and an altered $K_m$. The invention is not bound by a particular shuffling strategy only that at least one nucleotide sequence of the invention, or part thereof, is involved in such a shuffling strategy. Shuffling may involve only nucleotide sequences disclosed herein or may additionally involve shuffling any other nucleotide sequences known in the art including, but not limited to, GenBank Accession Nos. U04364, U04365, and U04366. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272: 336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The amino acid sequences of the invention can be used to isolate corresponding sequences from other organisms, particularly other arthropods. In this manner, methods such as PCR, hybridization, and the like can be used to identify nucleotide sequences encoding such amino acid sequences based on their sequence homology to the sequences set forth herein. Sequences isolated based on their sequence identity to the entire sequences set forth herein or to fragments thereof are encompassed by the present invention. Such sequences include sequences that are orthologs of the disclosed sequences. By "orthologs" genes are intended that are derived from a common ancestral gene and which are found in different species as a result of speciation. Genes found in different species are considered orthologs when their nucleotide sequences and/or their encoded polypeptide sequences share substantial identity as defined elsewhere herein. Functions of orthologs are often highly conserved among species. Thus, isolated sequences that encode for an orally active, pesticidal protein and which hybridize under stringent conditions to the pesticidal sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique among the sequences of the invention and are at least about 10 nucleotides in length, and preferably at least about 20 nucleotides in length. Such probes may be used to amplify corresponding sequences from a chosen organism by PCR. This technique may be used to isolate additional coding sequences from a desired organism or as a diagnostic assay to determine the presence of coding sequences in a an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" conditions are intended under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than about 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode a polypeptide of the invention and which hybridize under stringent conditions to the sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a polypeptide of the invention. BLAST polypeptide searches can be performed with the BLASTX program, score=50, wordlength=3, to obtain amino acid sequences homologous to a polypeptide or polypeptides of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for polypeptides) can be used. See http://www.ncbi.hhn.nih.gov. Alignment may also be performed manually by inspection.

Unless otherwise stated, nucleotide sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. For amino acid sequences, amino acid sequence identity values provided herein refer to the value obtained using GAP Version 10 using the following parameters: % identity using GAP Weight of 8 and Length Weight of 2, or any equivalent program. By "equivalent program" any sequence comparison program is intended that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for polypeptide sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

For purposes of the present invention, comparison of nucleotide or polypeptide sequences for determination of percent sequence identity to the sequences disclosed herein is preferably made using the GAP program in the Wisconsin Genetics Software Package (Version 8 or later) or any equivalent program. For GAP analyses of nucleotide sequences, a GAP Weight of 50 and a Length of 3 was used.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of polypeptides encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein.

The nucleotide constructs, nucleotide molecules and nucleotide sequences of the invention additionally encompass all complementary forms of such constructs, molecules and sequences. Further, the nucleotide constructs, nucleotide molecules and nucleotide sequences of the present invention encompass all nucleotide constructs, molecules and sequences which can be employed in the methods of the present invention for transforming plants including, but not limited to, those comprised of deoxyribonucleotides, ribonucleotides and combinations thereof. Such deoxyribonucleotides and ribonucleotides include both naturally occurring molecules and synthetic analogues. The nucleotide constructs, nucleotide molecules and nucleotide sequences of the invention also encompass all forms of nucleotide constructs including, but not limited to, single-stranded forms, double-stranded forms, hairpins, stem-and-loop structures and the like.

A further embodiment of the invention relates to a transformed organism, preferably a transformed organism selected from the group consisting of plant and insect cells, fungi, and baculoviruses, comprising a DNA molecule of the invention, an expression cassette comprising said DNA molecule or a vector molecule comprising said expression cassette, preferably stably incorporated into the genome of the transformed organism.

The sequences of the invention are provided in expression cassettes for expression in the organism of interest, for example a plant of interest. The cassette will include 5' and 3' regulatory sequences operably linked to a sequence of the invention. By "operably linked" a functional linkage is intended between a first sequence, such as a promoter, and a second sequence, wherein the promoter sequence initiates and mediates transcription of the DNA sequence corresponding to the second sequence. Generally, operably linked means that the nucleic acid sequences being linked are contiguous and, where necessary to join two polypeptide coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the sequence to be under the transcriptional regulation of the regulatory regions. The expression cassette may additionally contain selectable marker genes.

The expression cassette will include in the 5'-3' direction of transcription, a transcriptional and translational initiation region (i.e., promoter), a DNA sequence of the invention, and a transcriptional and translational termination region (i.e., termination region) functional in the host organism, for example, a plant. The promoter may be native or analogous, or foreign or heterologous, to the host and/or to the DNA sequence of the invention. Additionally, the promoter may be the natural sequence or alternatively a synthetic sequence. Where the promoter is "foreign" or "heterologous" to the host, it is intended that the promoter is not found in the native host organism into which the promoter is introduced. Where the promoter is "foreign" or "heterologous" to the DNA sequence of the invention, it is intended that the promoter is not the native or naturally occurring promoter for the operably linked DNA sequence of the invention. While it may be preferable to express the DNA sequences of the invention using heterologous promoters, the native promoter sequences may be used where functional in the host. As used herein, a chimeric gene comprises a coding sequence operably linked to a transcription initiation region that is heterologous to the coding sequence.

The termination region may be native with the transcriptional initiation region, may be native with the operably linked DNA sequence of interest, may be native with the host organism, or may be derived from another source (i.e., foreign or heterologous to the promoter, the DNA sequence of interest, the host organism, or any combination thereof). Convenient transcriptional and translational termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host. For example, the genes can be synthesized using plant-preferred codons for improved expression in plants. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding polypeptide (BiP) (Macejak et al. (1991) *Nature* 353:90-94); untranslated leader from the coat polypeptide mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

The expression cassettes may also contain sequences that act to enhance proper folding or secretion. Proper folding or secretion may be achieved by targeting operably linked polypeptides to organelles where such modifications occur. Modifying organelles include but are not limited to the endoplasmic reticulum and the Golgi Apparatus. Sequences known to target operably linked polypeptides to an appropriate organelle include, but are not limited to, the sporamin signal sequence, the barley alpha amylase sequence, and the vacuolar retention signal.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611, which are incorporated herein by reference.

Depending on the desired outcome, it may be beneficial to express the gene from an inducible promoter. Of particular interest for regulating the expression of the nucleotide sequences of the present invention in plants are wound-inducible promoters. Such wound-inducible promoters may respond to damage caused by insect feeding, and include potato polypeptidase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323: 73-76); MPI gene (Corderok et al. (1994) *Plant J.* 6(2):141-150); and the like, herein incorporated by reference.

Additionally, pathogen-inducible promoters may be employed in the methods and nucleotide constructs of the present invention. Such pathogen-inducible promoters include those from pathogenesis-related polypeptides (PR polypeptides), which are induced following infection by a pathogen; e.g., PR polypeptides, SAR polypeptides, beta-1, 3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal polypeptide expression within a particular plant tissue. See, for example, Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, by methods known in the art, for weak expression.

Vascular tissue-preferred promoters are known in the art. See for example copending Application No. 60/305,362, filed Jul. 13, 2001, herein incorporated by reference in its entirety. Vascular tissue preferred promoters allow tissue-preferred expression of nucleotide sequences of interest in the vasculature of plants. Vascular tissue preferred expression of pesticidal agents allows targeting of sucking insect pests in particular.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

"Seed-preferred" promoters include both "seed-specific" promoters (those promoters active during seed development such as promoters of seed storage polypeptides) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177 and U.S. Pat. No. 6,225,529; herein incorporated by reference). Gama-zein is a preferred endosperm-preferred promoter. Glob-1 is a preferred embryo-preferred promoter. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed and herein incorporated by reference.

Where low level expression is desired, weak promoters will be used. Low level expression is particularly desirable when expression of a polypeptide of the invention in a plant has a deleterious effect on the plant. Generally, by "weak promoter" is intended a promoter that drives expression of a coding sequence at a low level. By low level is intended at levels of about $1/1000$ transcripts to about $1/100,000$ transcripts to about $1/500,000$ transcripts. Alternatively, it is recognized that weak promoters also encompass promoters that are expressed in only a few cells and not in others to give a total low level of expression. Where a promoter drives expression at unacceptably high levels, portions of the promoter sequence can be deleted or modified to decrease expression levels.

Weak constitutive promoters include, for example the core promoter of the Rsyn7 promoter (WO 99/43838 and U.S. Pat. No. 6,072,050), the core 35S CaMV promoter, and the like.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) *Ph.D. Thesis*, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) *Ph.D. Thesis*, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. Protocols that are useful for transformation of rice plants in particular include biolistic methods (see Nayak et al. (1997) *Proc. Natl. Acad. Sci.* 94:2111-2116 and Christou, P. (1997) *Plant Mol. Biol.* 35:197-203) and *Agrobacterium* mediated methods (see Hiei et al. (1994) *Plant J.* 6:271-282 and Ishida et al. (1996) *Nat. Biotechnol.* 14:745-750).

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the protein of interest of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved. In addition, the desired genetically altered trait can be bred into other plant lines possessing other desirable characteristics using conventional breeding methods and/or top-cross technology.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the heterologous coding sequences of the two parental plants can be selected from all of the progeny by standard methods available in the art as described infra for selecting transformed plants. If necessary, the selected progeny can be used as either the pollen donor or pollen recipient in a subsequent cross-pollination.

Parts of transgenic plants within the scope of the invention comprise, for example, plant cells, protoplasts, tissues, callus, embryos as well as flowers, stems, fruits, leaves, roots originating in transgenic plants, and their progeny previously transformed with a DNA molecule of the invention and therefore consisting at least in part of transgenic cells. The invention further relates to plant propagating material of a transformed plant of the invention including, but not limited to, seeds, tubers, corms, bulbs, leaves and cuttings of roots and shoots.

The present invention may be used for transformation of any plant species, including, but not limited to, monocots and dicots. Examples of plants of interest include, but are not limited to, rice (*Oryza sativa*), corn (*Zea mays*), *Brassica* sp. (e.g., *B. napus, B. rapa, B. juncea*), particularly those *Brassica* species useful as sources of seed oil, alfalfa (*Medicago sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), flax (*Linum usitatissimum*), castor (*Ricinus communis*), palm (*Cycadophyta*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables of interest include tomatoes (*Lycopersicon esculentum*), lettuce (e.g., *Lactuca sativa*), green beans (*Phaseolus vulgaris*), garden beans, lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals of interest include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinusponderosa*), lodgepole pine (*Pinus contorta*), and Monterey pine (*Pinus radiata*); Douglas fir (*Pseudotsuga menziesii*); Western hemlock (*Tsuga canadenensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants including grain plants that provide seeds of interest, oil-seed plants, and leguminous plants (for example, rice, corn, alfalfa, sunflower, *Brassica*, soybean, rye, barley, cotton, safflower, peanut, sorghum, wheat, millet, tobacco, etc.). Leguminous plants include beans and peas. Beans include guar, locust bean, fenugreek, cowpea, mung bean, fava bean, lentils, chickpea, etc. More preferably, plants of the present invention are corn, rice, and soybean plants, yet more preferably rice plants.

In an embodiment, a transformed plant of the invention may be treated with a protectant coating. Components of the protectant coating include, but are not limited to, anti-desiccants, herbicides, insecticides, fungicides, bactericides, nematocides, and molluscicides. The protectant coating may include carriers, surfactants or application-promoting adjuvants. The protectant coating may be applied to seeds either by impregnating tubers or grains with a liquid formulation or by coating them with a combined wet or dry formulation. A transformed seed of the invention may be treated with a seed protectant coating comprising a seed treatment compound including, but not limited to, captan, carboxin, thiram, methalaxyl, and pirimiphos-methyl. An embodiment of the invention is a seed protectant coating comprising a pesticidal composition of the invention. In addition, in special cases, other methods of application to plants are possible, e.g. treatment directed at the buds or the fruit.

In an embodiment, host cells expressing the polypeptides of the invention are applied to the environment of the target pest or pests. The host cells may be treated to prolong the activity of the polypeptide of the invention. Host cells may be obtained from organisms such as, but not limited to, fungi, yeast, plants, mammals, and insects. Host organisms include, but are not limited to, bacteria, fungi, and eukaryotic organisms. Hosts of particular interest are the lower eukaryotes, such as fungi including *Phycomycetes* and *Ascomycetes*, and yeast, such as *Saccharomyces* and *Schizosaccharromyces*; and *Basidiomycetes* yeast, such as *Rhodotorula, Aureobasidium, Sporobolomyces*.

Hosts that natively produce detrimental substances and express a polypeptide of the invention are used at application levels below the threshold for undesirable effects.

Numerous ways for introducing a gene expressing a pesticidal polypeptide of the invention into a microorganism host under conditions allowing stable maintenance and expression of the gene exist. For example, expression cassettes can be constructed that include the nucleotide constructs of interest operably linked with the transcriptional and translational regulatory signals for expression of the nucleotide constructs, and a nucleotide sequence homologous with a sequence in the host organism, whereby integration will occur, and/or a replication system which is functional in the host, whereby integration or stable maintenance will occur.

Alternatively, polypeptides of the invention are produced by introducing a heterologous gene into a cellular host. Expression of the heterologous gene results, directly or indirectly, in the intracellular production and maintenance of a polypeptide of the invention. The cells are treated under conditions that prolong the activity of the polypeptide of the invention produced in the cell. The transgenic host cell expresses a polypeptide of the invention that retains pesticidal activity. These naturally encapsulated pesticidal polypeptides may then be formulated in accordance with conventional techniques for application to the environment hosting a target pest, e.g., soil, water, and foliage of plants. See, for example EPA 0192319, and the references cited therein.

Transcriptional and translational regulatory signals necessary for the expression of the heterologous gene include, but are not limited to, promoters, transcriptional initiation start sites, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

It is recognized that with these nucleotide sequences, antisense constructions, which are complementary to at least a portion of the messenger RNA (mRNA) for the orally active pesticidal sequences, can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

It is further recognized that the genes encoding the pesticidal polypeptides of the present invention can be used to transform insect pathogenic organisms such as baculoviruses. Of particular interest are recombinant baculoviruses expressing the nucleic acid molecules of the invention. Such recombinant baculovirus expression vectors may be prepared by protocols known to those skilled in the art (e.g., Tomalski et al., U.S. Pat. No. 5,266,317; McCutchen et al. (1991) *Bio/Technology* 9:848-852; Maeda et al. (1991) *Virology* 184: 777-780; also see O'Reilly et al. (1992) *Baculovirus Expression Vectors: A Laboratory Manual*, W. H. Freeman and Company, New York; King and Possee (1992) *The Baculovirus Expression System*, Chapman and Hall, London; U.S. Pat. No. 4,745,051; Ernst et al. (1994) *Nuc. Acid Res.* 22: 2855-2856; and WO 94/28114; herein incorporated by reference). Also of particular interest are the phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans* expressing the nucleic acid molecules of the invention.

One of skill in the art can design and prepare recombinant baculoviruses wherein a polypeptide of the invention is produced at appropriate times during infection, expressed in toxic quantities, and available for binding to target cells within the insect host. Expression of the polypeptide of the invention can be confirmed using a bioassay, LCMS, antibodies, or other methods known to one of skill in the art. The pesticidal effect of the polypeptides of the invention can be monitored in vivo. In vivo assays compare biological activity of recombinant viruses to wild-type viruses. Insect larvae can be infected orally by consumption of diet that contains test or control viruses and the larvae monitored for behavioral changes and mortality.

Characteristics of particular interest in selecting a host cell or host organism for purposes of production of a polypeptide of the invention include ease of introducing the pesticidal polypeptide gene into the host, availability of expression systems, efficiency of expression, stability of the polypeptide in the host, and the presence of auxiliary genetic capabilities. Characteristics of interest for use of a polypeptide of the invention as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

The transformed microorganisms of the invention include whole organisms, tissues, cells, spore(s), living or dead cells and cell components including mixtures of living and dead cells and cell components, including disrupted cells and cell components, or an isolated pesticidal polypeptide. The living or dead cells and cell components, mixtures of living and dead cells and cell components, including disrupted cells and cell components, or an isolated polypeptide can be formulated with an acceptable carrier into a composition that is, for example, a suspension, a solution, an emulsion, a dusting powder, a dispersible granule, a wettable powder, and an emulsifiable concentrate, an aerosol, an impregnated granule, an adjuvant, a coatable paste, and encapsulations in, for example, polymer substances.

Such compositions may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bactericides, nematocides, molluscicides, acaracides, plant growth regulators, harvest aids and fertilizers, can be combined with carriers, surfactants or adjuvants employed in the art of formulation or other components to facilitate product handling and application for particular target pests. Suitable carriers and adjuvants useful in the present invention can be solid or liquid and correspond to the substances employed in formulation technology including, but not limited to, natural or regenerated mineral substances, solvents, dispersants, wetting agents, tackifiers, binders or fertilizers. Compositions containing the active ingredients of the present invention can be applied to the crop area or plant to be treated alone, simultaneously, or in succession with other compounds. Methods of applying an active ingredient of the present invention or an agrochemical composition of the present invention which contains at least one of the pesticidal polypeptides of the present invention include, but are not limited to, foliar application, seed coating and soil application.

Suitable surface-active agents useful in the present invention include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkyl-naphtalene sulfonates, e.g. butyl-naphthalene sulfonate; salts of sulfonated naphthalene-formaldehyde condensates; salts of sulfonated phenol-formaldehyde condensates; more complex sulfonates such as the amide sulfonates, e.g. the sulfonated condensation product of oleic acid and N-methyl taurine; or the dialkyl sulfosuccinates, e.g., sodium sulfonate or dioctyl succinate. Non-ionic agents useful in the present invention include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of cationic surface-active agents useful in the present invention include, for instance, an aliphatic mono-, di, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials useful in the present invention include but are not limited to inorganic minerals such as kaolin, phyllosilicates, carbonates, sulfates, phosphates or botanical materials such as cork, powdered corncobs, peanut hulls, rice hulls, and walnut shells.

The compositions of the present invention can be in a form suitable for direct application or as a concentrate of a primary composition that requires dilution with a suitable quantity of water or other diluent before application. The pesticidal concentration will vary depending upon the nature of the particular formulation, specifically, whether it is a concentrate or it is to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb-5.0 lb. per acre when in dry form and at about 0.01 pts.-10 pts. per acre when in liquid form.

In a further embodiment, the compositions, as well as the transformed microorganisms and pesticidal polypeptides, of the invention can be treated prior to formulation to prolong the pesticidal activity when applied to the environment of a target pest. Such treatment can be by chemical and/or physical means. Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason, Animal Tissue Techniques, W.H. Freeman and Co., 1967).

The compositions, including the transformed microoganisms and pesticidal polypeptides, of the invention can be applied to the environment of an insect pest by, for example, spraying, atomizing, dusting, scattering, coating or pouring, introducing into or on the soil, introducing into irrigation water, by seed treatment or general application. In an embodiment, a polypeptide of the invention is applied prophylactically, at times such as, but not limited to, prior to the appearance of a pest, in early stages of infestation, and in late stages of infestation. The compositions of the invention may be applied at any stage of plant development including, but not limited to, pre-germination, post-germination, budding, flowering, ripening, pre-harvest, concomitant with harvest, and post-harvest. The compositions of the invention may contain additional insecticides if desired. One embodiment of the invention is a granular form of a composition comprising an agrochemical such as, for example, herbicides, insecticides, fertilizers, inert carriers, and dead cells of a transformed microorganism of the invention.

The invention is drawn to compositions and methods for inducing resistance in a plant to plant pests. Accordingly, the compositions and methods are also useful in protecting plants against fungal pathogens, viruses, nematodes, insects and the like.

By "disease resistance" it is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. By "altered pest resistance" it is intended that the organism with the altered resistance differs from wild type or untreated organisms in its susceptibility to damage from pests. By "altered insect resistance" it is intended that the organism differs from wild type or untreated organisms in its susceptibility to damage from insect pests. The substance or organism with an altered pest resistance will differ from a wild-type or untreated organism in it susceptibility to damage from pests by at least about 5% to about 50%, at least about 10% to about 60%, at least about 30% to about 70%, at least about 40% to about 80%, or at least about 50% to about 90% or greater.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference).

Methods of rearing insect larvae and performing bioassays are well known to one of ordinary skill in the art. General procedures include addition of the experimental compound or organism to the diet source in an enclosed container. Bioassays may be performed as described in Czapla and Lang (1990) *J. Econ. Entomol.* 83(6): 2480-2485, herein incorporated by reference, and as described elsewhere herein. Pesticidal activity targeting insects is tested on larval, immature, or adult stage insect pests. The insects may be reared in total darkness at from about 20° C. to about 30° C. and from about 30% to about 70% relative humidity. Pesticidal activity can be measured by factors such as, but not limited to, mortality, weight loss, attraction, repellency and other behavioral and/ or physical changes after feeding and exposure to the pesticidal composition of the present invention.

Pathogens of the invention include, but are not limited to, viruses or viroids, bacteria, insects, nematodes, fungi, acarids, protozoan pathogens and animal-parasitic liver flukes and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthephaseolorum* var. *sojae* (*Phomopsis sojae*), *Diaporthephaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata, Soybean mosaic virus, Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium alboatrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagnospora meliloti, Stemphylium botryosum, Leptotrochila medicaginis;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Tilletia indica, Pythium graminicola,* High Plains Virus, European wheat striate virus; Sunflower: *Plasmophora halstedii, Sclerotinia sclerotiorum, Aster Yellows, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudomonas avenae, Erwinia chrysanthemi* p.v. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Periconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*),

*Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthora macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The embodiments of the present invention may be effective against a variety of pests. Target pests include, but are not limited to, insect pests. "Insect pests" is intended to include insects and other similar pests such as, for example, those of the order Acari including, but not limited to, mites and ticks. Insect pests of the present invention include, but are not limited to, insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails,* and *Yponomeuta padella.*

Embodiments of the present invention may be effective against Hemiptera such as, but not limited to, *Lygus hesperus, Lygus lineolaris, Lyguspratensis, Lygus rugulipennis Popp, Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara viridula, Eurygaster, Coreidae, Pyrrhocoridae, Tinidae, Blostomatidae, Reduviidae,* and *Cimicidae.*

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Homoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* sugarcane borer; *Diabrotica virgifera,* western corn rootworm; *Diabrotica longicornis barberi,* northern corn rootworm; *Diabrotica undecimpunctata howardi,* southern corn rootworm; *Melanotus* spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; *Eleodes, Conoderus,* and *Aeolus* spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus* leucopterus, chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *Zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonomus grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplus femurrubrum,* redlegged grasshopper; *Melanoplus differentialis,* differential grasshopper; *Thrips tabaci,* onion thrips; *Frankliniella fusca,* tobacco thrips; *Tetranychus cinnabari-* nus, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhopper; *Blissus leucopterus* leucopterus, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus* leucopterus, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* spp., Root maggots.

Arthropod venom may be obtained through a variety of methods known in the art, including but not limited to, dissection and isolation of the venom gland and milking of the venom (Gopalakrishnakone et al. (1995) *Lab Anim.* 29:456-458, herein incorporated by reference).

Compositions of the invention include antibodies that selectively bind a polypeptide of the invention. Antibodies specific to the polypeptides of the invention are prepared by standard immunological techniques known to those skilled in the art. See Harlow et al. (1988) *Antibodies: A Laboratory Manual*, Cold Spring Harbor, N.Y.; Sanbrook et al. (1989) *Molecular Cloning: A Laboratory Manual* ($2^{nd}$ d. ed., Cold Spring Harbor Laboratory Press, Plain View, N.Y. and Ausubel et al., eds (1995) *Current Protocols in Molecular Biology*, Wiley Interscience, New York, herein incorporated by reference in their entirety.

Many peptides isolated from venoms modulate ion-channels. Ion channels comprise a family of proteins classified according to their biophysical and pharmacological characteristics. Modulation of ion channel activity is known to affect the central nervous system of mammals and other organisms. An embodiment of the invention comprises the use of a composition of the invention to modulate ion channel activity in mammals. An orally active polypeptide of the invention may cross gut or nasal passages of mammals. The compositions of the invention may be used to treat heart and neurological diseases (e.g. U.S. Pat. No. 4,925,664; U.S. Application No. 60/105,404; U.S. Application No. 60/140,227; and U.S. Application No. 60/110,590).

Another embodiment involves the use of the compositions of the invention in the treatment and preservation of textiles. Insect pests devalue and destroy textiles and fabrics including, but not limited to, carpets, draperies, clothing, blankets, and bandages. The compositions of the invention may be applied to finished textile products or may be expressed in plants yielding fibers that are incorporated into fabrics. Insect pests that attack textiles include, but are not limited to, webbing clothes moths and carpet beetles.

The following examples are presented by way of illustration, not by way of limitation.

EXPERIMENTAL

Example 1

Fractionation of Polypeptides from Arthropod Venom

Polypeptides were enriched from arthropod venom using a variety of HPLC chromatography conditions. Crude arthropod venom was applied to either HP1100 or Microbore LC columns as indicated. The peptides were resolved using a method set forth herein. The fractions were assayed for pesticidal activity as described elsewhere herein.

For all HPLC chromatography methods Solvent A consists of 95% Water and Solvent B consists of 95% acetonitrile with either 0.1% TFA or HFBA as noted.

For gradients over HP1100 columns a 0.6 mL/min flow rate was used unless otherwise noted.

| METHOD 1: | 60% Solvent B in 70 minutes TFA; C4 column |
|---|---|
| METHOD 2: | 60% Solvent B in 70 minutes TFA; C4 column 0.325 mL/minute flow rate |
| METHOD 3: | 15-50% Solvent B in 70 minutes HFBA; C4 column |

For gradients over Microbore LC columns a 50 µL/minute flow rate was used unless otherwise noted.

| METHOD 4: | 60% Solvent B in 70 minutes TFA; C4 column |
|---|---|
| METHOD 5: | 30% Solvent B in 60 minutes TFA; C4 column |
| METHOD 6: | 15-45% Solvent B in 65 minutes HFBA; C18 column |
| METHOD 7: | 50% Solvent B in 70 minutes TFA; C4 column |
| METHOD 8: | 10-75% Solvent B in 70 minutes HFBA; C18 column |
| METHOD 9: | 40% Solvent B in 70 minutes HFBA; C18 column |
| METHOD 10: | 15-15% Solvent B in 70 minutes HFBA; C18 column |

Example 2

Protein Sequencing

Purified peptides were reduced with 10 mM dithiothreitol and alkylated with 4-vinylpyridine. The reduced and alkylated peptide was then isolated from the chemicals on a Magic 2002 Microbore LC using reversed phase chromatography. Protein sequencing was performed on an Applied Biosystems Procise 494 protein sequencer utilizing the Edman degradation reaction. Isolated peptides were pipetted onto a pre-filtered glass fiber filter from Applied Biosystems containing 100 mM Biobrene. The filter was dried and the cartridge was re-assembled and placed onto the Procise 494. N-terminal sequencing was determined with the pulsed-liquid method standard with the Procise 494. Data were collected and analyzed on the Model 610A data analysis program from Applied Biosystems.

Example 3

Full Length Peptide Sequencing

Purified peptides were reduced and alkylated as mentioned previously. The peptides were then digested with GluC and LysC endoproteinases from Boehringer-Mannheim. These endoproteinases cleave on the C-terminal side of glutamic acid and lysine respectively in the peptide. Peptide fragments were collected on the Magic 2002 Microbore LC using reversed phase chromatography. Each individual peptide was sequenced as described previously until a full-length sequence map was obtained.

Example 4

Mass Spectroscopy Analysis

Mass spectroscopy analysis was performed on a Micromass Platform LCZ electrospray instrument. The peptide was either analyzed by LC/MS utilizing the Magic 2002 Microbore LC and reversed phase chromatography or the purified peptide was directly injected into the mass spec. probe. One of skill in the art will recognize that a variety of conditions may be utilized for LC/MS. Mass spectroscopy analysis of the present peptides was performed under the following conditions: Capillary voltage=4.3, Cone voltage=60, Extractor voltage=4, Source Block temperature=100, Desolvation Temperature=200, Low Mass Resolution=12.5, High Mass Resolution=12.5, Ion Energy=0.9, and Multiplier=650. Data was analyzed on Micromass MassLynx software. The protein was deconvoluted using MaxEnt and the accurate mass obtained.

Example 5

Southern Corn Rootworm Droplet Feeding Bioassay

This method assays the effects of polypeptides from crude and fractionated venoms on first instar *Diabrotica undecimpunctata howardi* (southern corn rootworm).

Southern corn rootworm (SCR), *Diabrotica undecimpunctata howardii*, eggs were collected in the rearing chamber and placed in a zip lock bag at 28° C. in the dark. After hatching, the larvae were incubated for 48 hours prior to testing.

On the day of testing, fifteen circles of parafilm that approximately fit the inner diameter of a 15×60 mm glass petri dish bottom were cut. Ten to fifteen circles of James River Verigood™ blotter were prepared. A damp blotter circle was placed in the inner lid of a polystyrene petri dish. The blotter served as the mat or base of the test unit.

2 mg of the freeze-dried polypeptides were suspended in 100 µl of 5% sucrose/0.04% blue dye FD&C #1. The resuspended polypeptide was stored on ice and used in a timely manner.

Three or more replicates of at least 10 insects per replicate were performed on each test compound. A no compound control containing only 5% sucrose/0.04% FD&C#1 blue dye was also performed.

The parafilm circles were placed in the bottom of the Pyrex glass petri dish and 3-5 µl aliquots of the polypeptide solution were placed in a ring-like fashion on the parafilm. Sample desiccation was prevented with the top of the Pyrex dish.

Ten insects were placed in the center of the circle of polypeptide aliquots. Larvae were handled one at a time to insure injury-free larvae. Once the larvae were in the circle of droplets, the larvae were forced to feed by pushing the heads into the solution. When the entire gut of the larvae was blue, the larvae were removed and placed in the polystyrene dish with the damp blotter. Ten larvae were transferred for each replicate. The larvae were rinsed with a droplet of $dH_2O$ to prevent any sucrose or polypeptides on the insect from influencing the activity of the larvae.

Insects were closely observed for the first minutes. The accurate time of the appearance of symptoms was determined with a stopwatch. Paralysis was detected by rolling larvae on their backs. Inability to right themselves, contracted movements, and sluggish behavior were also signs of intoxication. After 15 minutes, the test unit was capped. Larvae were observed again at 30, 60, and 120 minutes. Insects were scored on the characteristics of paralysis, lethargy, and contractedness at various intervals after treatment. Insects fed crude and fractionated venoms exhibited a significantly greater degree of paralysis, lethargy and contractedness than controls. In some cases mortality was observed in the insects fed the crude and fractionated venoms.

Example 6

Homopteran Membrane Feeding Bioassay for Screening Polypeptides

This assay can be used for a variety of homopterans including, but not limited to, *Myzus persicae* and *Perigrinus maidis*. The assay involves trapping the sample between two layers of maximally stretched parafilm which act as a sachet on top of a small vessel containing the insect of choice.

The assay was prepared as follows: 1 cm diameter polystyrene tubing was cut into 15 mm lengths. One end of the tube was then capped with a fine mesh screen. Five insects were then added to the chamber after which the first layer of parafilm was stretched over the remaining open end. 25 µl of sample (polypeptide in a 5% sucrose solution containing McCormick green food coloring) was then placed on top of the stretched parafilm. A second layer of parafilm was then stretched by hand and placed over the sample. The sample was spread between the two layers of parafilm to make a continuous sachet on which the insects fed. The sachet was then covered tightly with saran wrap to prevent evaporation and produce a slightly pressurized sample. The assay tubes were monitored for insect reproduction and death on a 24 hour basis and compared to a 5% sucrose control. Insects fed crude and fractionated venoms exhibited a significantly greater degree of mortality and significantly less reproduction than controls.

Example 7

Construction of Recombinant Baculovirus Expressing Pesticidal Polypeptides

The cDNAs encoding the instant polypeptides were introduced into the baculovirus genome itself. For this purpose the cDNAs were placed under the control of the polyhedrin promoter. The IE1 promoter or any other one of the baculovirus promoters may be suitable also. The cDNA, together with appropriate leader sequences was then inserted into a baculovirus transfer vector using standard molecular cloning techniques. Following transformation of *E. coli* DH5α, isolated colonies were chosen and plasmid DNA was prepared and analyzed by restriction enzyme analysis. Colonies containing the appropriate fragment were isolated, propagated, and plasmid DNA was prepared for cotransfection.

Example 8

Expression of Pesticidal Polypeptides in Insect Cells

Spodoptera frugiperda cells (Sf-9) were propagated in ExCell® 401 media (JRH Biosciences, Lenexa, Kans.) supplemented with 3.0% fetal bovine serum. Lipofectin® (50 µL at 0.1 mg/mL, Gibco/BRL) was added to a 50 µL aliquot of the transfer vector containing the toxin gene (500 ng) and linearized polyhedron-negative AcNPV (2.5 µg, Baculogold® viral DNA, Pharmigen, San Diego, Calif.). Sf-9 cells (approximate 50% monolayer) were co-transfected with the viral DNA/transfer vector solution. The supernatant fluid from the co-transfection experiment was collected at 5 days post-transfection and recombinant viruses were isolated employing standard plaque purification protocols, wherein only polyhedron-positive plaques were selected (O'Reilly et al. (1992), *Baculovirus Expression Vectors: A Laboratory Manual*, W. H. Freeman and Company, New York.). Sf-9 cells in 35 mM petri dishes (50% monolayer) were inoculated with 100 µL of a serial dilution of the viral suspension, and supernatant fluids were collected at 5 days post infection. In order to prepare larger quantities of virus for characterization, these supernatant fluids are used to inoculate larger tissue cultures for large scale propagation of recombinant viruses.

Expression of the encoded toxin gene by the recombinant baculovirus was confirmed using a bioassay, LCMS, or antibodies. The presence of toxin activity in the recombinant viruses was monitored in vivo. These assays involve comparison of biological activity of recombinant viruses to wild-type viruses. Third instar larvae of *H. virescens* were infected orally by consumption of diet that contains test and control viruses and the larvae were monitored for behavioral changes and speed of kill. Larvae fed test viruses exhibited a significantly faster speed of kill than larvae fed control viruses.

Isolated plugs of a standard insect diet were inoculated with approximately 5000 PIBs of each virus. Individual larvae that had not fed for 12 h prior to beginning of the bioassay were allowed to consume the diet for 24 h. The larvae were transferred to individual wells in a diet tray and monitored for symptoms and mortality on a daily basis (Zlotkin et al. (1991) *Biochimie* (Paris) 53:1073-1078). Again, larvae fed test viruses exhibited a significantly faster speed of kill than larvae fed control viruses.

Example 9

Construction of CV1 Expression Vectors

A synthetic version of CV1 with a barley alpha amylase signal peptide (SEQ ID NO:5) was constructed with a codon bias representative of *Oryza sativa* using standard molecular biology methods. See Ausubel et al., eds. (1995) *Current Protocols in Molecular Biology*, (Greene Publishing and Wiley-Interscience, New York) and Sambrook et al. (1989) *Molecular Cloning: A Laboratory Manual* (2d ed., Cold Spring Harbor Laboratory Press, Plainview, N.Y.). The barley alpha amylase (BAA) signal sequence was added to the 5' end of a nucleotide sequence corresponding to the mature amino terminus of the CV1 peptide. The BAA signal peptide targets operably linked polypeptides to the endoplasmic reticulum (ER), where the polypeptide undergoes proper folding and subsequent secretion out of the cell (Rahmatullah, et al (1989) *Plant Mol. Biol.* The codon usage database used to determine a codon bias representative of *Oryza sativa* is found in Table 1.

TABLE 1

*Streptomyces coelicolor* A3(2) [gbbct]: 6257 CDS's (2043281 codons)
fields: [triplet] [frequency: per thousand] ([number])

| UUU | 0.4 (863) | UCU | 0.6 (1266) | UAU | 1.0 (1962) | UGU | 0.7 (1448) |
|---|---|---|---|---|---|---|---|
| UUC | 26.0 (53065) | UCC | 20.2 (41262) | UAC | 19.5 (39789) | UGC | 7.0 (14341) |
| UUA | 0.1 (128) | UCA | 1.0 (2137) | UAA | 0.1 (290) | UGA | 2.4 (4878) |
| UUG | 2.4 (4935) | UCG | 13.8 (28229) | UAG | 0.5 (1089) | UGG | 15.1 (30770) |
| CUU | 1.5 (3129) | CCU | 1.5 (2995) | CAU | 1.6 (3366) | CGU | 5.5 (11183) |
| CUC | 36.6 (74736) | CCC | 25.4 (51951) | CAC | 21.5 (44018) | CGC | 39.1 (79956) |
| CUA | 0.3 (657) | CCA | 1.3 (2633) | CAA | 1.3 (2593) | CGA | 2.5 (5124) |
| CUG | 61.3 (125241) | CCG | 33.6 (68652) | CAG | 25.1 (51248) | CGG | 32.0 (65332) |
| AUU | 0.6 (1228) | ACU | 1.1 (2347) | AAU | 0.7 (1436) | AGU | 1.5 (3030) |
| AUC | 27.6 (56340) | ACC | 39.6 (80826) | AAC | 16.2 (33191) | AGC | 12.3 (25187) |
| AUA | 0.7 (1367) | ACA | 1.6 (3194) | AAA | 1.0 (2041) | AGA | 0.8 (1574) |
| AUG | 15.8 (32271) | ACG | 18.9 (38697) | AAG | 19.7 (40293) | AGG | 3.7 (7488) |
| GUU | 1.4 (2905) | GCU | 2.9 (5908) | GAU | 2.9 (6024) | GGU | 9.3 (18920) |
| GUC | 47.2 (96460) | GCC | 78.6 (160548) | GAC | 58.0 (118595) | GGC | 61.4 (125467) |
| GUA | 2.7 (5416) | GCA | 5.3 (10890) | GAA | 8.5 (17445) | GGA | 7.1 (14608) |
| GUG | 35.3 (72144) | GCG | 49.8 (101831) | GAG | 48.5 (99056) | GGG | 18.2 (37288) |

Coding GC 72.38% 1st letter GC 72.74% 2nd letter GC 51.39% 3rd letter GC 93.00%

The synthetic gene was constructed using a series of overlapping complementary oligonucleotides. The complementary oligonucleotides were annealed, and the Klenow enzyme was used to fill in the gaps. The full length gene was PCR amplified using primers corresponding to the 5' and 3' ends of the gene sequence. Restriction sites were incorporated into the 5' ends of the PCR primers. The amplified product was TOPO cloned into pCR2.1 (Invitrogen), and the BAA-CV1 sequence was confirmed.

The BAA-CV1 fragment was subcloned into an expression vector containing an appropriate promoter, such as the root-preferred IFS1 (isloflavone synthase 1) promoter (copending U.S. Application Ser. Nos. 60/278,379, filed Mar. 23, 2001, and 60/311,461, filed Aug. 10, 2001, herein incorporated by reference) and the UCP1 promoter (U.S. application Ser. No. 09/556,163 and U.S. Pat. No. 6,072,050, herein incorporated by reference). The restriction sites introduced during PCR amplification facilitated cloning of the nucleic acid molecule behind the promoter of interest. The soybean-derived, root-preferred IFS promoter directs expression of the CV1 peptide in root tissue, the natural site of soybean cyst nematode feeding. The UCP1 promoter is a constitutive, root-preferred promoter. Additionally, the IFS vector contains the NOS termination sequence.

Example 10

Construction of Aam1 Expression Vector

A synthetic version of Aam1 with a sweet potato sporamin signal peptide (SEQ ID NOS:14, 15, and 16) was constructed using overlapping oligonucleotides as described above herein. The codon bias of the synthetic sequence was representative of *Oryza sativa*. Selection of codons was based on the Kazusa codon usage database. The sweet potato sporamin (SP) signal sequence was added to the 5'end of a nucleotide sequence corresponding to the mature amino terminus of the Aam1 peptide. The SP signal peptide (Hattori, et al (1985) *Plant Molecular Biology* 5:313-320) targets operably linked peptides to the ER and for export from the cell. Restriction sites were added during the cloning process to facilitate cloning behind the UCP1 promoter.

Example 11

Construction of VC1 Expression Vector

A synthetic version of VC1 with a PR1 signal peptide (SEQ ID NOS:12 and 13) was constructed using overlapping oligonucleotides as described above herein. The codon bias of the synthetic sequence was representative of *Oryza sativa*. Selection of codons was based on the Kazusa codon usage database. The PR1 signal sequence was added to the 5' end of a nucleotide sequence corresponding to the mature amino terminus of the VC1 peptide. The tobacco PR1 signal peptide (Cornellison, et al (1986) *Nature* 321:531-532) targets operably linked polypeptides to the ER for the purpose of proper folding and disulfide bridge formation and for subsequent export from the cell. Restriction sites were added during the cloning process to facilitate cloning behind the IFS1 promoter. Additionally, the IFS vector contains the NOS termination sequence.

Example 12

Construction of Aam1 Expression Vector for Maize Expression

A synthetic version of Aam1 with a BAA signal peptide (SEQ ID NOS:17, 18, and 19) was constructed using overlapping oligonucleotides as described above herein. The codon bias of the synthetic sequence was representative of *Streptomyces coelicolor*. The codon bias of *Streptomyces coelicolor* was chosen because of its overall similarity to codon usage in plants. Selection of codons was based on the Kazusa codon usage database. See Table 1. The BAA signal sequence was added to the 5' end of a nucleotide sequence corresponding to the mature amino terminus of the Aam1 peptide. The BAA signal peptide targets operably linked polypeptides to the endoplasmic reticulum (ER), where the polypeptide undergoes proper folding and subsequent secretion out of the cell (Rahmatullah, et al (1989) *Plant Mol. Biol.*, herein incorporated by reference).

The restriction sites introduced during PCR amplification facilitated cloning of the nucleic acid molecule behind a promoter of interest. The BAA-Aam1 fragment was subcloned into an expression vector containing an appropriate promoter, such as the maize ubiquitin promoter and the maize h2B promoter (U.S. Pat. No. 6,177,611, herein incorporated by reference). The ubiquitin promoter and the h2B promoter are strong constitutive promoters. Constitutive promoters were selected to allow testing of the effects of Aam1 expression in a multiplicity of tissues including, but not limited to, leaf, whorl, and roots. The expression vector further contains the pinII terminator sequence 3' to the nucleotide sequence of interest. Restriction sites flank the promoter:Aam1:pinII cassette and facilitate cloning of the expression cassette into binary plasmids for transformation.

Example 13

Identification of Ts7 and Assessment of Oral Activity cDNAs encoding potential sodium channel neurotoxins were identified from sequence data derived from a cDNA library of *Centruroides vittatus* telsons. The nucleotide sequences, including Ts7 (SEQ ID NO:21 and 23), exhibited homology to known toxins. Full length genes were PCR amplified with oligonucleotide primers introducing restriction enzyme sites at the 5' and 3' ends of the gene. The PCR products were TOPO-cloned into pCR2.1 (Invitrogen Co.) and the sequence was confirmed. The resulting constructs were then cloned into a binary vector between the Cauliflower mosaic virus 35S promoter and the NOS termination signal. The binary vector also contained a selection marker cassette including the Cauliflower mosaic 35S promoter, the BAR gene, and NOS terminator.

Binary constructs were electroporated into *Agrobacterium tumefaciens* strain C58. Transformed *Agrobacterium* cultures were grown in YM media for 2 days at 28° C. to an $OD_{600}$ of approximately 1.0. Cells were pelleted by centrifugation and resuspended at the original culture volume in 5% sucrose with 0.05% Silwet L-77. The *Agrobacterium* slurry was sprinkled onto the inflorescences of flowering *Arabidopsis thaliana* (Landberg) plants using a 10-25 ml pipette. The inflorescences were thoroughly soaked. Plants were covered with a humidity dome in the dark for 24 hours and were grown under normal conditions thereafter. Seeds were harvested six weeks later and were generously sown in flats filled with soil. Transgenic events were selected by herbicide treatment using BASTA and PCR confirmed. Those 3 week old events surviving BASTA treatments were tested in bioassays using *Myzus persicae* (Green Peach Aphid).

Bioassays were performed on individual transformation events enclosed within plastic tubes with a fine mesh screen at the top to confine the aphids. Adult aphids were applied to the base of each plant. Plants were scored for total number of adult aphids and nymphs at various intervals post infestation. Those events expressing Ts7 cDNA were found to exhibit a greater degree of aphid resistance than controls.

Example 14

Construction of Ts7 Expression Vector

A synthetic version of Ts7 with a BAA signal peptide (SEQ ID NO:25) was constructed using overlapping oligonucleotides as described above herein. The codon bias of the synthetic sequence was representative of *Streptomyces coelicolor* as described elsewhere herein. The BAA signal sequence was added to the 5' end of a nucleotide sequence corresponding to the mature amino terminus of the Ts7 peptide. The BAA signal peptide targets operably linked polypeptides to the endoplasmic reticulum (ER), where the polypeptide undergoes proper folding and subsequent secretion out of the cell (Rahmatullah, et al (1989) *Plant Mol. Biol.*, herein incorporated by reference).

The BAA-Ts7 fragment was subcloned into an expression vector containing an appropriate promoter, such as the maize ubiquitin promoter and the maize h2B promoter (U.S. Pat. No. 6,177,611, herein incorporated by reference). The restriction sites introduced during PCR amplification facilitated cloning of the nucleic acid molecule behind the promoter of interest. The ubiquitin promoter and the h2B promoter are strong constitutive promoters. Constitutive promoters were selected to allow testing of the effects of Ts7 expression in a multiplicity of tissues including, but not limited to, leaf, whorl, and roots. The expression vector further contains the pinII terminator sequence 3' to the nucleotide sequence of interest. Restriction sites flank the promoter:Ts7:pinII cassette and facilitate cloning of the expression cassette into binary plasmids for transformation.

Example 15

Transformation of Rice and Regeneration of Transgenic Rice Plants

Embryogenic (E) callus was obtained from the scutellum of immature and mature seed. Mature seeds were physically dehulled by applying pressure with a plastic microcentrifuge tube rack. Dehulled seeds were placed in a 50 ml tube. Seeds were sterilized by agitating them in 40 mls of 70% ethanol for 1.5 minutes. The seeds were rinsed twice with 40 mls of 20% bleach. 40 mls of 20% bleach were added to the seeds. The bleach and seed mixture was agitated at 25-50 rpm for 20 minutes. The bleach solution was poured away and the seeds were rinsed three times with 40 mls of sterile water. Two additional sterile water rinses were performed, each under agitation, and for a duration of 10 minutes then 15 minutes. Water was removed and the seeds were transferred into a sterile petri dish. 12-16 seeds were placed on each petri plate containing callus initiation media. Callus initiation media comprises MS salts, Nitsch and Nitsch vitamins, 1.0 mg/L 2,4-D and 10 µM $AgNO_3$. The plates were wrapped with fibertape and incubated in the dark at 27-28° C. for 18 days.

After 18 days a heterogeneous population of somatic pro-embryos and embryos proliferated from the scutellum. The callus initiated from the scutellum appears as a light-yellow bumpy outgrowth. The callus was subcultured every 2 weeks on callus maintenance media (CM) at a plating density of 100-200 mg/plate in a size distribution pattern of 0.5-1.0 mm pieces, 1 mM apart. CM comprises N6 salts, Nitsch and Nitsch vitamins, 1 mg/L 2,4-D (Chu, et al (1985) *Sci. Sinica* 18:659-668, herein incorporated by reference). During the culture period the phenotype of the callus changed. The callus lines were maintained as clonal populations and subcultured to perpetuate the desired E phenotype. A desired E phenotype is typified by callus clumps ranging in size between 0.1 and 0.5 mm. E callus is smooth and regular as opposed to non-embryogenic callus which displays a rough or jagged surface. E phenotype callus tensile quality may be described as spongy and is light yellow to white in color. E callus has a F.W. doubling time of 3-4 days. Generally, the E callus used in transformation was obtained from one subculture onto CM. Typically the E callus cultures were transformed within 3-10 weeks of initiation.

Good E callus was prepared for transformation as described below. Petri plates were prepared with CM medium in a circular diameter of about 4 cm and a #541 Whatman paper was placed on the CM medium. 0.5 ml of top agar were layered onto the Whatman paper. 0.5 to 1 mm pieces of E callus was transferred onto the top agar. The plates were sealed with fibertape and incubated in the dark at 27°-28° C. for 3-5 days in a 40-60% humidity environment. The filters with the callus pieces were transferred to CM supplemented with 0.5M osmoticum (0.25M mannitol plus 0.25M sorbitol) for 3 hours in the dark. The plates were placed in a flow-hood and the lids were left ajar for 20-45 minutes prior to bombardment.

Gold particles were weighed so that the final concentration was 60 mg/1 ml or 0.6 mM and placed in a sterile 1.5 ml siliconized microcentrifuge tube. The gold particles were washed with 1 ml of 100% ethanol, gently agitated for 3 minutes and sonicated for 10 seconds. The gold particles were pelleted by centrifugation. The supernatant was removed and the gold particles were washed twice with 1 ml of sterile double distilled water. The gold particles were resuspended in 1 ml of sterile double-distilled water. The gold suspension was sonicated for ten seconds and 50 µl aliquots were placed in 1.5 ml siliconized microcentrifuge tubes.

Plasmid DNA was precipitated onto the prepared gold particles in the following manner. The gold suspension was sonicated twice briefly. Approximately 8 µg of the trait gene and 2 µg of the hygromycin resistance (hpt) gene (a 2:1 molar ratio), 50 µl 2.5 M $CaCl_2$, and 20 µl 0.1 M spermidine were added to the gold suspension. The solution was mixed gently for 3 minutes, sonicated briefly, mixed for 30 seconds, and centrifuged. The supernatant was removed and the particles were washed twice with 1 ml 100% ethanol. The particles were resuspended in 50 µl 100% ethanol. The solution was finger vortexed several times and sonicated briefly to relieve clumps and disperse particles. The tubes were incubated at –70° C. for at least 30 minutes. The mixture was sonicated briefly. 6 µl of the DNA/Gold solution was dispensed and evaporated onto a mylar macrocarrier.

The callus-containing plates were bombarded with a PDS-1000/He Gun with the following parameters: 5-10 µg of total DNA precipitated onto 3 mg of 0.6 µM gold particles (from 50 µl prep), 8 cm from the stopping screen, 27-29 inches Hg vacuum, and 1050-1100 PSI He pressure. Each plate was bombarded twice.

Within an hour of bombardment, the filter paper supporting the callus was placed on CM plates. The plates were wrapped with fibertape and incubated in the dark at 27-28° C. for 3-5 days. After 3-5 days, the callus was transferred to a sterile 50 ml conical tube. The callus was weighed and cooled top agar was added at a concentration of 40 mg/ml. Clumps were disrupted with a 10 ml pipette. Three ml aliquots of the suspended callus were dispensed onto SM50 media. SM50 media is comprised of CM media containing 50 PPM hygromycin B. The plates were wrapped with fibertape and incubated in the dark at 27-28° C. for 4 weeks. After 4 weeks as transformation events appeared, they were transferred to SM50 and grown an additional two weeks. After two weeks, 8-10 mm clumps of the transformants were transferred to RM1 media. RM1 comprises MS salts, Nitsch and Nitsch vitamins, 2% sucrose, 3% sorbitol, 0.4% gelrite, and 50 PPM hygromycin B. The plates were wrapped in fibertape and incubated at 25° C. in the dark for approximately 3 weeks. The transformants were transferred to RM2 media. RM2 media is comprised of MS salts, Nitsch and Nitsch vitamins, 3% sucrose, 0.4% gelrite, and 50 PPM hygromycin B. The RM2 plates were incubated in cool white light (~40 $\mu E^{-1}$) with a 12 hour photoperiod at 25° C. and 30-40% humidity.

Plantlets emerged from the callus after 4-8 weeks on RM2 media. When the plantlets reached 2-3 cm they were gently transferred to RM3 media in phytatrays (Sigma Chemical Co., St. Louis, Mo.). RM3 media is comprised of ½ MS salts, Nitsch and Nitsch vitamins, 1% sucrose, and 50 PPM hygromycin B. 2-6 plantlets were transferred per phytatray. Clumps of the smaller plantlets were transferred to RM2 media for an additional 3 weeks before transfer to RM3 media.

After sufficient root and shoot growth occurred, the plants were transferred to a 24-spot tray containing Metromix. 3 plants per clone were potted. The plants were grown in a 12/12 light cycle at approximately 350 $\mu E^{-1}$ and 30° C.

Example 16

Assay of Trangenic Plants for Enhanced Pesticidal Resistance

For Homopteran whole plant bioassays, regenerated transgenic plants were assayed individually in single chamber containers composed of the 4 inch pot containing the plant and a flexible polystyrene sleeve capped with fine plastic mesh. An exact number of insects was added to the chamber and the chamber was sealed to prevent insect escape. At least three and preferably five regenerated control plants of equivalent age to the transformants were included in the experiment. Host plant resistance was assessed based on insect mortality and population increase. Resistance was defined as insect reproduction one standard deviation below the average reproduction within the control plants or insect mortality one standard deviation above the control plant average insect mortality. Transgenic plants were insect resistant.

For lepidopteran assays, 3 1 cm segments from a mature leaf of the regenerated plant were placed in three separate chambers of a 12 well microtiter plate. 3 neonate larvae were added to each chamber, and the chamber was sealed to prevent escape of the insects. As with the Homopteran assay, 3 to 5 control plants were assayed in a similar way for each experiment. Plant resistance was determined based on mortality and leaf damage in comparison to the control plant performance. Again, the transgenic plants were resistant.

In some assays the radish leaves used to rear *Myzus persicae* were placed at the base of the transgenic plant. The transgenic plant was enclosed in a plastic tube covered with a fine mesh top. As the radish leaf dried, the green peach aphids (*M. persicae*) moved from the radish leaf to the transgenic plants. The transgenic plants were resistant to *Myzus persicae* infestation and/or damage.

Example 17

Figure 14:
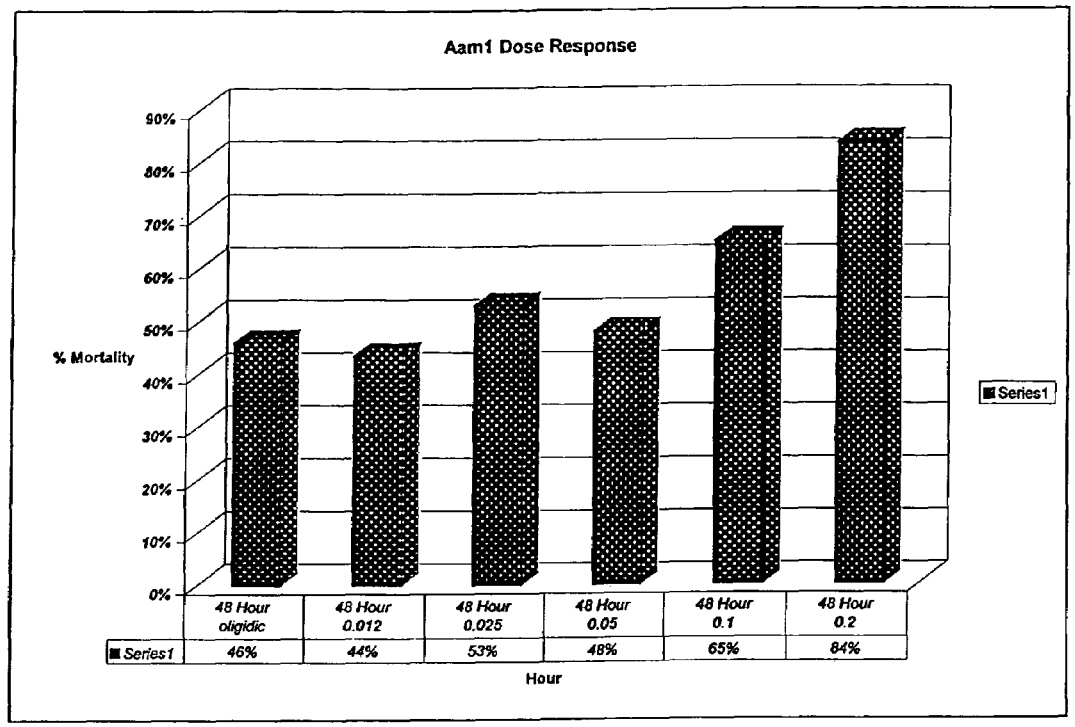
FIG. 14 depicts the results of a dose response assay of *Myzus persicae* to Aam1 (SEQ ID NO:20). The percent mortality of M persicae 48 hours after exposure to the indicated doses of Aam1 is presented. The Aam1 dose is in %, thus 1%=1 gm/100 ml, and 0.2%=2 mg/ml, 0.1%=1 mg/ml, 0.05%=0.5 mg/ml, 0.025%=0.25 mg/ml, 0.012%=0.12 mg/ml.

Leaf Segment Assay for Lepidopteran Activity: Identification of Aam1: a Homopteran and Lepidopteran Orally Active Peptide Initial screening of five minute fractions of the venom from Androctonus amoreuxi indicated activity against the corn plant hopper *Perigrinus maidis*. Initial activity was observed in Fraction 8. Based on this activity, Fraction 8 was further fractionated by HPLC (see Example 1 for conditions). The Homopteran activity was then found to be associated with Fraction 8-6. Sufficient quantities of this purified protein were collected to allow confirmation of activity and to initiate protein sequencing by Edmund degradation as described in Example 2. The mature sequence was determined to be that indicated in SEQ ID NO:20. Molecular weight of the mature peptide was confirmed by Mass spectroscopy to be 6534.5 Daltons. This information was used to create a synthetic gene codon biased for expression in rice. This synthetic gene was then cloned into the appropriate vector for transformation of rice as described in Example 15. A synthetic gene was also generated for expression in the *Pichia* yeast and baculovirus systems. Activity of expressed toxins from both systems was confirmed in Homopteran feeding assays. A dose response assay was performed on the aphid *Myzus persicae*. The results are found in FIG. 14.

Transformed rice was bioassayed for activity against *Aphis fabeae* by a combination choice, reproduction assay. Two transformant rice plants containing the 35S:Aam1 transgene were combined with 2 control plants in a large insect cage. Each plant was infested twice with 50 aphids and the aphids were allowed to move to their preferred plant. A second infestation was subsequently performed to increase infestation levels. 5 days later the plants were removed from the common cage and placed on an open shelf in water moats to prevent movement between plants. The plants were then monitored for insect population growth. Aphid populations on the control plants increased rapidly while the aphid populations on the transgenic plants grew relatively little and the aphids continued to disperse widely rather than settle near the mater and form foci of infestation as seen in the control plants (data not shown).

Lepidopteran activity was assessed in a leaf segment assay against ECB as described here. Substantial leaf protection was demonstrated in the 35S:Aam1 leaves. Microscopic observation also disclosed classic symptoms of paralysis among the ECB larvae.

Example 18

Transformation of Maize by Particle Bombardment and Regeneration of Transgenic Plants Immature maize embryos from greenhouse donor plants are bombarded with a plasmid containing a nucleotide sequence encoding a polypeptide of the invention operably linked to a ubiquitin promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence encoding a polypeptide of the invention operably linked to a ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 µl 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of the polypeptide of the invention by assays known in the art, such as, for example, insect feeding assays.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 19

*Agrobacterium*-Mediated Transformation of Maize and Regeneration of Transgenic Plants For *Agrobacterium*-mediated transformation of maize with a nucleotide sequence encoding a polypeptide of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the nucleotide sequence encoding a polypeptide of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 20

Soybean Embryo Transformation

Soybean embryos are bombarded with a plasmid containing a nucleotide sequence of the invention operably linked to a SCP1 promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures are maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising a nucleotide sequence of the invention operably linked to the SCP1 promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 21

Fluorescence Imaging Ratiometric Assay

Embryonic neuronal cultures of the American cockroach *Periplaneta americana* were established following the method of Beadle and Lees (See Beadle D. J. and Lees G., Chapter 5 in *Cell Culture Approaches to Invertebrate Neuroscience*, Beadle, D. J., Lees, G. and Kater, S. B. (eds.) Academic Press, New York 1988) with minor modification. Briefly, 24-day old oothecae were collected, surface-sterilized and cut open one third below the dorsal midline. The heads were then removed and placed in Schneider's *Drosophila* medium. Using fine forceps 32 brains were individually removed and placed in a small glass vial containing 790 µl of '5+4' medium. The brains were dissociated using a Pasteur pipette with tip flamed to slightly less than half its original diameter. A 5 µl volume of the suspension was placed at the center of each well of a poly-L-lysine coated 96-well plate. After cells were allowed to attach, wells were filled with a 1:1 mixture of Leibovitz's L-15 medium and Yunker's modified Grace's medium in which 20-hydroxyecdysone was added. Cells were maintained in a high humidity incubator at 29° C. until testing.

Cells were rinsed in standard physiological saline having the following composition (mM): NaCl 190; $CaCl_2$ 9; KCl 3.1; probenicid 1; Tris buffer 10; pH 7.2. Cells were then bathed in saline containing the calcium sensitive fluoroprobe Fluo-4 AM (2 µM) and Pluronic F127 (0.002%) for 45 minutes then rinsed in saline for at least 15 minutes prior to testing. (One could also use Fluo-3 AM, Fura-2 AM or other calcium-sensitive fluoroprobes). The 96-well plate was placed on a computer-controlled stage mounted onto a Nikon Diaphot microscope and imaged using a 20× Fluor objective (NA 0.75). Individual wells from the 96-well plate were sequentially excited with light at 495 nm and the emitted fluorescence at 530 nm detected using a Hamamatsu ORCA ER digital camera.

Acquisition control, image processing and image analysis were conducted using Universal Imaging Corporation's MetaMorph™ imaging software. A series of "control" images were obtained for each well. Test and control compounds were added directly to each well via a multi-channel pipettor (one could use an automated fluidic system) and subsequent "treated" images were obtained. Subsequently, post-acquisition image processing was performed consisting of the following operations. A threshold with respect to minimum gray level was set for all images in order to facilitate image morphometry. Individual cells were separated and identified based on meeting designated morphometric criteria for total size and shape as previously determined experimentally for this cell type. Regions of interest were generated from the periphery of each identified cell and the mean pixel value for each region was generated for each control and treated image. Compound-stimulated increase in intracellular free calcium concentration resulted in an increase of Fluo-4 fluorescence emission. The application of Aam1 to the neuronal cells resulted in changes in fluorescence characteristic of a sodium channel agonist. This confirms that Aam1 likely acts at the level of the sodium channel.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule having a nucleotide sequence selected from the group consisting of:
   (a) a nucleotide sequence encoding a polypeptide comprising the amino acid sequence set forth in SEQ ID NO:20;
   (b) a nucleotide sequence comprising the coding sequence set forth in nucleotides 73-249 of SEQ ID NO:17 or nucleotides 64-240 of SEQ ID NO:14;
   (c) a nucleotide sequence encoding a polypeptide having at least 95% sequence identity to the amino acid sequence set forth in SEQ ID NO:20, wherein said polypeptide retains pesticidal activity against insect pests of the Homopteran or Lepidopteran orders; and
   (d) a nucleotide sequence having at least 95% sequence identity to the coding sequence set forth in nucleotides 73-249 of SEQ ID NO:17 or nucleotides 64-240 of SEQ ID NO:14, wherein said nucleotide sequence encodes a polypeptide having pesticidal activity against insect pests of the Homopteran or Lepidopteran orders.

2. An expression cassette comprising a nucleic acid molecule of claim 1, wherein said nucleotide sequence is operably linked to a promoter.

3. The expression cassette of claim 2, wherein said promoter is selected from the group consisting of constitutive, inducible, and tissue-preferred promoters.

4. The expression cassette of claim 2, wherein said promoter is a vascular tissue-preferred promoter.

5. A host cell expressing a polypeptide encoded by any one of the nucleic acid molecules of claim 1.

6. The host cell of claim 5, wherein the host cell is selected from the group consisting of fungi, yeast, plant, mammal, and insect cells.

7. A virus comprising the isolated nucleic acid of claim 1.

8. A recombinant baculovirus expression vector comprising a nucleotide sequence encoding a polypeptide having the amino acid sequence set forth in SEQ ID NO:20.

9. A recombinant baculovirus expression vector comprising a nucleotide sequence encoding a polypeptide consisting of at least 10 contiguous amino acids of SEQ ID NO:20.

10. A transformed plant comprising in its genome at least one stably incorporated expression cassette comprising a nucleotide sequence operably linked to a promoter that drives expression in a plant cell, wherein said nucleotide sequence is selected from the group consisting of:
   (a) a nucleotide sequence encoding a polypeptide comprising the amino acid sequence set forth in SEQ ID NO:20;
   (b) a nucleotide sequence comprising the coding sequence set forth in nucleotides 73-249 of SEQ ID NO:17 or nucleotides 64-240 of SEQ ID NO:14;
   (c) a nucleotide sequence encoding a polypeptide having at least 95% sequence identity to the amino acid sequence set forth in SEQ ID NO:20, wherein said polypeptide retains pesticidal activity against insect pests of the Homopteran or Lepidopteran orders; and
   (d) a nucleotide sequence having at least 95% sequence identity to the coding sequence set forth in nucleotides 73-249 of SEQ ID NO:17 or nucleotides 64-240 of SEQ ID NO:14, wherein said nucleotide sequence encodes a polypeptide having pesticidal activity against insect pests of the Homopteran or Lepidopteran orders.

11. The transformed plant of claim 10, wherein said promoter is selected from the group consisting of constitutive, inducible, and tissue-preferred promoters.

12. The transformed plant of claim 10, wherein said promoter is a vascular tissue-preferred promoter.

13. The transformed plant of claim 10, wherein said promoter is an insect-inducible promoter.

14. The transformed plant of claim 10, wherein said plant is a crop plant selected from the group consisting of maize, wheat, sorghum, rice, barley, soybean, alfalfa, sunflower, *Brassica*, and tomato.

15. The transformed plant of claim 14, wherein said crop plant is rice.

16. A transformed seed of the plant of claim 10, comprising in its genome said at least one stably incorporated expression cassette.

17. The transformed plant of claim 10, wherein said promoter is a vascular tissue-preferred promoter, said plant is rice, and said nucleotide sequence encodes the polypeptide set forth in SEQ ID NO:20 (Aam1).

18. The plant of claim 10, wherein said plant exhibits altered insect resistance.

19. The plant of claim 18, wherein said insect resistance is impacting insects selected from the group consisting of Homopteran and Lepidopteran species.

20. A method for altering plant insect pest resistance, said method comprising stably transforming into a plant cell a nucleotide sequence operably linked to a promoter that drives expression in said plant cell, and regenerating a plant from said plant cell, wherein said nucleotide sequence comprises a nucleotide sequence selected from the group consisting of:
   (a) a nucleotide sequence encoding a polypeptide comprising the amino acid sequence set forth in SEQ ID NO:20;
   (b) a nucleotide sequence comprising the coding sequence set forth in nucleotides 73-249 of SEQ ID NO:17 or nucleotides 64-240 of SEQ ID NO:14;
   (c) a nucleotide sequence encoding a polypeptide having at least 95% sequence identity to the amino acid sequence set forth in SEQ ID NO:20, wherein said polypeptide retains pesticidal activity against insect pests of the Homopteran or Lepidopteran orders; and
   (d) a nucleotide sequence having at least 95% sequence identity to the coding sequence set forth in nucleotides 73-249 of SEQ ID NO:17 or nucleotides 64-240 of SEQ ID NO:14, wherein said nucleotide sequence encodes a polypeptide having pesticidal activity against insect pests of the Homopteran or Lepidopteran orders.

21. The method of claim 20, wherein said promoter is selected from the group consisting of constitutive, inducible, and tissue-preferred promoters.

22. The method of claim 20, wherein said promoter is a vascular tissue-preferred promoter.

23. The method of claim 20, wherein said promoter is an insect-inducible promoter.

24. The method of claim 20, wherein said promoter is a vascular tissue preferred promoter, said plant is rice, said nucleotide sequence encodes the polypeptide set forth in SEQ ID NO:20 (Aam1), and said plant possesses altered insect resistance to both Homopteran and Lepidopteran species of insects.

25. The method of claim 24, wherein said Lepidopteran species of insect is resistant to a Bt toxin.

26. The method of claim 20, wherein said plant is a crop plant selected from the group consisting of maize, wheat, sorghum, rice, barley, soybean, alfalfa, sunflower, *Brassica*, and tomato.

27. The method of claim 20, wherein said insect resistance impacts insects selected from the group consisting of Homoptera; and Lepidoptera.

28. The nucleic acid molecule of claim 1, wherein said nucleotide sequence encoding said polypeptide further comprises an operably linked sequence encoding a signal peptide.

29. The nucleic acid molecule of claim 28, wherein said polypeptide comprises the amino acid sequence set forth in SEQ ID NO:20, and said nucleotide sequence comprises the sequence set forth in SEQ ID NO:17 or SEQ ID NO:14.

30. The transformed plant of claim 10, wherein said nucleotide sequence encoding said polypeptide further comprises an operably linked sequence encoding a signal peptide.

31. The transformed plant of claim 30, wherein said polypeptide comprises the amino acid sequence set forth in SEQ ID NO:20, and said nucleotide sequence comprises the sequence set forth in SEQ ID NO:17 or SEQ ID NO:14.

32. The method of claim 20, wherein said nucleotide sequence encoding said polypeptide further comprises an operably linked sequence encoding a signal peptide.

33. The method of claim 32, wherein said polypeptide comprises the amino acid sequence set forth in SEQ ID NO:20, and said nucleotide sequence comprises the sequence set forth in SEQ ID NO:17 or SEQ ID NO:14.

* * * * *

SEQUENCE LISTING

<160> NUMBER OF SEQ ID NOS: 27

<210> SEQ ID NO 1
<211> LENGTH: 355
<212> TYPE: DNA
<213> ORGANISM: Centruroides vittatus
<220> FEATURE:
<221> NAME/KEY: CDS
<222> LOCATION: (49)...(303)
<220> FEATURE:
<221> NAME/KEY: misc_feature
<222> LOCATION: (0)...(0)
<223> OTHER INFORMATION: CV1

<400> SEQUENCE: 1

```
ggatccccg ggctgcagga gaatttatac gttatcagaa aactcaaa atg aat tat        57
                                                    Met Asn Tyr
                                                      1 ttt ata ttg att ttg gtt gca gct cta tta ata ttg gat gca aat tgt      105
Phe Ile Leu Ile Leu Val Ala Ala Leu Leu Ile Leu Asp Ala Asn Cys
      5                  10                  15 aag aaa gac gga tat cca gtt gat gcg gag gaa tgt aga tat aat tgt      153
Lys Lys Asp Gly Tyr Pro Val Asp Ala Glu Glu Cys Arg Tyr Asn Cys
 20                  25                  30                  35 tgg aaa aac gaa tac tgc gac aaa atc tgc aaa gag aag aaa ggt gaa      201
Trp Lys Asn Glu Tyr Cys Asp Lys Ile Cys Lys Glu Lys Lys Gly Glu
                 40                  45                  50 agt gga tat tgt tac gga tgg aat ctg tcg tgt tgg tgt ata ggt ctt      249
Ser Gly Tyr Cys Tyr Gly Trp Asn Leu Ser Cys Trp Cys Ile Gly Leu
             55                  60                  65 cct gat gat aca aat aca aaa atg aat ccc ttt tgt cag ggt ttg gat      297
Pro Asp Asp Thr Asn Thr Lys Met Asn Pro Phe Cys Gln Gly Leu Asp
         70                  75                  80 ggg taa acgaaattta accaataaaa aaaaaaaaa ggggaaatct gcttttacta        353
Gly * at                                                                   355
```

<210> SEQ ID NO 2
<211> LENGTH: 84
<212> TYPE: PRT
<213> ORGANISM: Centruroides vittatus

<400> SEQUENCE: 2

```
Met Asn Tyr Phe Ile Leu Ile Leu Val Ala Ala Leu Leu Ile Leu Asp
  1               5                  10                  15

Ala Asn Cys Lys Lys Asp Gly Tyr Pro Val Asp Ala Glu Glu Cys Arg
             20                  25                  30

Tyr Asn Cys Trp Lys Asn Glu Tyr Cys Asp Lys Ile Cys Lys Glu Lys
         35                  40                  45

Lys Gly Glu Ser Gly Tyr Cys Tyr Gly Trp Asn Leu Ser Cys Trp Cys
     50                  55                  60

Ile Gly Leu Pro Asp Asp Thr Asn Thr Lys Met Asn Pro Phe Cys Gln
 65                  70                  75                  80

Gly Leu Asp Gly
```

<210> SEQ ID NO 3
<211> LENGTH: 255
<212> TYPE: DNA
<213> ORGANISM: Centruroides vittatus
<220> FEATURE:

```
<221> NAME/KEY: CDS
<222> LOCATION: (1)...(255)

<400> SEQUENCE: 3 atg aat tat ttt ata ttg att ttg gtt gca gct cta tta ata ttg gat     48
Met Asn Tyr Phe Ile Leu Ile Leu Val Ala Ala Leu Leu Ile Leu Asp
 1               5                  10                  15 gca aat tgt aag aaa gac gga tat cca gtt gat gcg gag gaa tgt aga     96
Ala Asn Cys Lys Lys Asp Gly Tyr Pro Val Asp Ala Glu Glu Cys Arg
             20                  25                  30 tat aat tgt tgg aaa aac gaa tac tgc gac aaa atc tgc aaa gag aag    144
Tyr Asn Cys Trp Lys Asn Glu Tyr Cys Asp Lys Ile Cys Lys Glu Lys
         35                  40                  45 aaa ggt gaa agt gga tat tgt tac gga tgg aat ctg tcg tgt tgg tgt    192
Lys Gly Glu Ser Gly Tyr Cys Tyr Gly Trp Asn Leu Ser Cys Trp Cys
 50                  55                  60 ata ggt ctt cct gat gat aca aat aca aaa atg aat ccc ttt tgt cag    240
Ile Gly Leu Pro Asp Asp Thr Asn Thr Lys Met Asn Pro Phe Cys Gln
 65                  70                  75                  80 ggt ttg gat ggg taa                                                255
Gly Leu Asp Gly *

<210> SEQ ID NO 4
<211> LENGTH: 64
<212> TYPE: PRT
<213> ORGANISM: Centruroides vittatus

<400> SEQUENCE: 4

Lys Lys Asp Gly Tyr Pro Val Asp Ala Glu Glu Cys Arg Tyr Asn Cys
 1               5                  10                  15

Trp Lys Asn Glu Tyr Cys Asp Lys Ile Cys Lys Glu Lys Lys Gly Glu
             20                  25                  30

Ser Gly Tyr Cys Tyr Gly Trp Asn Leu Ser Cys Trp Cys Ile Gly Leu
         35                  40                  45

Pro Asp Asp Thr Asn Thr Lys Met Asn Pro Phe Cys Gln Gly Leu Asp
 50                  55                  60

<210> SEQ ID NO 5
<211> LENGTH: 267
<212> TYPE: DNA
<213> ORGANISM: Artificial Sequence
<220> FEATURE:
<223> OTHER INFORMATION: Codon biased nucleotide sequence encoding CV1.
      Codon biased for rice.
<220> FEATURE:
<221> NAME/KEY: CDS
<222> LOCATION: (73)...(267)
<220> FEATURE:
<221> NAME/KEY: sig_peptide
<222> LOCATION: (1)...(72)
<223> OTHER INFORMATION: BAA signal peptide

<400> SEQUENCE: 5 atg gcc aac aag cac ctc tcc ctg agc ctt ttc ttg gtg ctc cta ggc     48
Met Ala Asn Lys His Leu Ser Leu Ser Leu Phe Leu Val Leu Leu Gly
            -20                 -15                 -10 ctg tcg gcg tct tta gct tca ggg aag aaa gac ggc tac ccg gtg gat     96
Leu Ser Ala Ser Leu Ala Ser Gly Lys Lys Asp Gly Tyr Pro Val Asp
         -5                   1               5 gcc gag gaa tgc cgc tat aac tgt tgg aag aat gag tac tgc gac aag    144
Ala Glu Glu Cys Arg Tyr Asn Cys Trp Lys Asn Glu Tyr Cys Asp Lys
     10                  15                  20 atc tgc aag gag aaa aag ggg gaa tcc gga tac tgt tat ggc tgg aac    192
Ile Cys Lys Glu Lys Lys Gly Glu Ser Gly Tyr Cys Tyr Gly Trp Asn
```

```
Ile Cys Lys Glu Lys Lys Gly Glu Ser Gly Tyr Cys Tyr Gly Trp Asn
 25                  30                  35                  40 ctc agc tgc tgg tgc att ggc ctg ccc gat gac acc aat acg aag atg    240
Leu Ser Cys Trp Cys Ile Gly Leu Pro Asp Asp Thr Asn Thr Lys Met
             45                  50                  55 aac cca ttc tgc cag ggg ctt gat tga                                267
Asn Pro Phe Cys Gln Gly Leu Asp  *
         60

<210> SEQ ID NO 6
<211> LENGTH: 375
<212> TYPE: DNA
<213> ORGANISM: Leiurus quinquestriatus
<220> FEATURE:
<221> NAME/KEY: CDS
<222> LOCATION: (38)...(298)
<220> FEATURE:
<221> NAME/KEY: misc_feature
<222> LOCATION: (0)...(0)
<223> OTHER INFORMATION: LghIV
<220> FEATURE:
<221> NAME/KEY: misc_feature
<222> LOCATION: 18, 33, 374
<223> OTHER INFORMATION: n = A,T,C or G

<400> SEQUENCE: 6
gaattcggca cctcgtgnaa tttcggcaca gtncaaa atg aat tac ttg atg ata    55
                                         Met Asn Tyr Leu Met Ile
                                           1               5 att agt ttg gct ctt ctt cta atg aca ggt gtg gag agc ggt gta cgt    103
Ile Ser Leu Ala Leu Leu Leu Met Thr Gly Val Glu Ser Gly Val Arg
             10                  15                  20 gat gct tat att gcc gac gat aaa aac tgt gtg tac act tgt ggt gca    151
Asp Ala Tyr Ile Ala Asp Asp Lys Asn Cys Val Tyr Thr Cys Gly Ala
             25                  30                  35 aat tca tat tgc aac aca gaa tgt acc aag aac ggt gct gag agt ggc    199
Asn Ser Tyr Cys Asn Thr Glu Cys Thr Lys Asn Gly Ala Glu Ser Gly
     40                  45                  50 tat tgt caa tgg ttt ggt aaa tat gga aat gcc tgc tgg tgc ata aag    247
Tyr Cys Gln Trp Phe Gly Lys Tyr Gly Asn Ala Cys Trp Cys Ile Lys
 55                  60                  65                  70 ttg ccc gat aaa gta cct att aga ata cca gga aag tgc cgt ggc cga    295
Leu Pro Asp Lys Val Pro Ile Arg Ile Pro Gly Lys Cys Arg Gly Arg
                 75                  80                  85 taa atttaagatg aatataacc taaatataac tgttaaataa atataattta           348
 * aaaatttaaa aaaaaaaaaa aaaaanc                                       375

<210> SEQ ID NO 7
<211> LENGTH: 86
<212> TYPE: PRT
<213> ORGANISM: Leiurus quinquestriatus

<400> SEQUENCE: 7

Met Asn Tyr Leu Met Ile Ile Ser Leu Ala Leu Leu Leu Met Thr Gly
  1               5                  10                  15

Val Glu Ser Gly Val Arg Asp Ala Tyr Ile Ala Asp Asp Lys Asn Cys
                 20                  25                  30

Val Tyr Thr Cys Gly Ala Asn Ser Tyr Cys Asn Thr Glu Cys Thr Lys
             35                  40                  45

Asn Gly Ala Glu Ser Gly Tyr Cys Gln Trp Phe Gly Lys Tyr Gly Asn
         50                  55                  60
```

-continued

```
Ala Cys Trp Cys Ile Lys Leu Pro Asp Lys Val Pro Ile Arg Ile Pro
 65                  70                  75                  80

Gly Lys Cys Arg Gly Arg
                85
```

<210> SEQ ID NO 8
<211> LENGTH: 261
<212> TYPE: DNA
<213> ORGANISM: Leiurus quinquestriatus
<220> FEATURE:
<221> NAME/KEY: CDS
<222> LOCATION: (1)...(261)
<220> FEATURE:
<221> NAME/KEY: misc_feature
<222> LOCATION: (0)...(0)
<223> OTHER INFORMATION: LghIV

<400> SEQUENCE: 8

```
atg aat tac ttg atg ata att agt ttg gct ctt ctt cta atg aca ggt      48
Met Asn Tyr Leu Met Ile Ile Ser Leu Ala Leu Leu Leu Met Thr Gly
  1               5                  10                  15 gtg gag agc ggt gta cgt gat gct tat att gcc gac gat aaa aac tgt      96
Val Glu Ser Gly Val Arg Asp Ala Tyr Ile Ala Asp Asp Lys Asn Cys
             20                  25                  30 gtg tac act tgt ggt gca aat tca tat tgc aac aca gaa tgt acc aag     144
Val Tyr Thr Cys Gly Ala Asn Ser Tyr Cys Asn Thr Glu Cys Thr Lys
         35                  40                  45 aac ggt gct gag agt ggc tat tgt caa tgg ttt ggt aaa tat gga aat     192
Asn Gly Ala Glu Ser Gly Tyr Cys Gln Trp Phe Gly Lys Tyr Gly Asn
     50                  55                  60 gcc tgc tgg tgc ata aag ttg ccc gat aaa gta cct att aga ata cca     240
Ala Cys Trp Cys Ile Lys Leu Pro Asp Lys Val Pro Ile Arg Ile Pro
 65                  70                  75                  80 gga aag tgc cgt ggc cga taa                                         261
Gly Lys Cys Arg Gly Arg *
                85
```

<210> SEQ ID NO 9
<211> LENGTH: 483
<212> TYPE: DNA
<213> ORGANISM: Vaejovis carolinanus
<220> FEATURE:
<221> NAME/KEY: CDS
<222> LOCATION: (65)...(358)
<220> FEATURE:
<221> NAME/KEY: misc_feature
<222> LOCATION: (0)...(0)
<223> OTHER INFORMATION: VC1

<400> SEQUENCE: 9

```
gccgctctag aactagtgga tccccgggc tgcaggtttc tccgtttgga taatcgtcta     60 gaaa atg aac gct aaa ata act gtt cta ttt ttc ctc gta gcc att aca    109
     Met Asn Ala Lys Ile Thr Val Leu Phe Phe Leu Val Ala Ile Thr
       1               5                  10                  15 att gct tct tgt gcc tgg ata agt gag aaa aaa gtt caa gat gtc att    157
Ile Ala Ser Cys Ala Trp Ile Ser Glu Lys Lys Val Gln Asp Val Ile
             20                  25                  30 gat aaa aaa ttg cca aac gga atg gtg aag aat gca atc aaa gcc gta    205
Asp Lys Lys Leu Pro Asn Gly Met Val Lys Asn Ala Ile Lys Ala Val
         35                  40                  45 gta cac aaa gca gcg aag aat aag cac ggc tgt ttt gct gat ttt gat    253
Val His Lys Ala Ala Lys Asn Lys His Gly Cys Phe Ala Asp Phe Asp
     50                  55                  60 gta gga gga gga tgc gaa cag cac tgc cag aaa acg gaa agt aaa gca    301
Val Gly Gly Gly Cys Glu Gln His Cys Gln Lys Thr Glu Ser Lys Ala
```

```
Val Gly Gly Gly Cys Glu Gln His Cys Gln Lys Thr Glu Ser Lys Ala
         65                  70                  75 gga atc tgt cac gga acc aaa tgc aaa tgc ggt att ccc cgt gcc tat     349
Gly Ile Cys His Gly Thr Lys Cys Lys Cys Gly Ile Pro Arg Ala Tyr
 80                  85                  90                  95 aaa aaa taa atcactgatt aatgctaacg gtgaatacat ataatatttc             398
Lys Lys * tatccaagct ttagtcaaaa ataataaaat gaattatttg cacacttaca ttctatgtaa   458
tatacacaaa ataaatcgaa tttgg                                         483
```

```
<210> SEQ ID NO 10
<211> LENGTH: 97
<212> TYPE: PRT
<213> ORGANISM: Vaejovis carolinanus

<400> SEQUENCE: 10

Met Asn Ala Lys Ile Thr Val Leu Phe Phe Leu Val Ala Ile Thr Ile
 1               5                  10                  15

Ala Ser Cys Ala Trp Ile Ser Glu Lys Lys Val Gln Asp Val Ile Asp
             20                  25                  30

Lys Lys Leu Pro Asn Gly Met Val Lys Asn Ala Ile Lys Ala Val Val
         35                  40                  45

His Lys Ala Ala Lys Asn Lys His Gly Cys Phe Ala Asp Phe Asp Val
     50                  55                  60

Gly Gly Gly Cys Glu Gln His Cys Gln Lys Thr Glu Ser Lys Ala Gly
 65                  70                  75                  80

Ile Cys His Gly Thr Lys Cys Lys Cys Gly Ile Pro Arg Ala Tyr Lys
                 85                  90                  95

Lys

<210> SEQ ID NO 11
<211> LENGTH: 294
<212> TYPE: DNA
<213> ORGANISM: Vaejovis carolinanus
<220> FEATURE:
<221> NAME/KEY: CDS
<222> LOCATION: (1)...(294)
<220> FEATURE:
<221> NAME/KEY: misc_feature
<222> LOCATION: (0)...(0)
<223> OTHER INFORMATION: VC1

<400> SEQUENCE: 11 atg aac gct aaa ata act gtt cta ttt ttc ctc gta gcc att aca att    48
Met Asn Ala Lys Ile Thr Val Leu Phe Phe Leu Val Ala Ile Thr Ile
 1               5                  10                  15 gct tct tgt gcc tgg ata agt gag aaa aaa gtt caa gat gtc att gat    96
Ala Ser Cys Ala Trp Ile Ser Glu Lys Lys Val Gln Asp Val Ile Asp
             20                  25                  30 aaa aaa ttg cca aac gga atg gtg aag aat gca atc aaa gcc gta gta   144
Lys Lys Leu Pro Asn Gly Met Val Lys Asn Ala Ile Lys Ala Val Val
         35                  40                  45 cac aaa gca gcg aag aat aag cac ggc tgt ttt gct gat ttt gat gta   192
His Lys Ala Ala Lys Asn Lys His Gly Cys Phe Ala Asp Phe Asp Val
     50                  55                  60 gga gga gga tgc gaa cag cac tgc cag aaa acg gaa agt aaa gca gga   240
Gly Gly Gly Cys Glu Gln His Cys Gln Lys Thr Glu Ser Lys Ala Gly
 65                  70                  75                  80 atc tgt cac gga acc aaa tgc aaa tgc ggt att ccc cgt gcc tat aaa   288
Ile Cys His Gly Thr Lys Cys Lys Cys Gly Ile Pro Arg Ala Tyr Lys
```

```
                           85                  90                  95
aaa taa                                                                     294
Lys *

<210> SEQ ID NO 12
<211> LENGTH: 312
<212> TYPE: DNA
<213> ORGANISM: Artificial Sequence
<220> FEATURE:
<221> NAME/KEY: CDS
<222> LOCATION: (76)...(312)
<221> NAME/KEY: sig_peptide
<222> LOCATION: (1)...(75)
<223> OTHER INFORMATION: PR1 signal peptide
<220> FEATURE:
<223> OTHER INFORMATION: Codon biased nucleotide sequence encoding VC1.
      Codon biased for rice.

<400> SEQUENCE: 12 atg aac ttc ctc aag tcc ttt ccg ttc tac gcc

-continued

<210> SEQ ID NO 14
<211> LENGTH: 240
<212> TYPE: DNA
<213> ORGANISM: Artificial Sequence
<220> FEATURE:
<223> OTHER INFORMATION: Codon biased nucleotide sequence encoding Aam1.
      Codon biased rice.
<220> FEATURE:
<221> NAME/KEY: CDS
<222> LOCATION: (64)...(240)
<220> FEATURE:
<221> NAME/KEY: sig_peptide
<222> LOCATION: (1)...(63)
<223> OTHER INFORMATION: Sweet potato sporamin signal

<400> SEQUENCE: 14

```
atg aag gcc ttc acc ctc gcg ctg ttt ctc gct ctc tcc ttg tat ctt        48
Met Lys Ala Phe Thr Leu Ala Leu Phe Leu Ala Leu Ser Leu Tyr Leu
    -20                 -15                 -10 ctc ccc aac cca gcg gct gac gtc ccg gga aac tac cca ctt gat tct        96
Leu Pro Asn Pro Ala Ala Asp Val Pro Gly Asn Tyr Pro Leu Asp Ser
 -5                  1               5                  10 tcc gac aat acc tac ctg tgc gcc cct ttg gga gat aat ccg gac tgc       144
Ser Asp Asn Thr Tyr Leu Cys Ala Pro Leu Gly Asp Asn Pro Asp Cys
             15                  20                  25 att aag atc tgt cag aaa cac ggt gtg gat tac ggg tat tgc tac gcc       192
Ile Lys Ile Cys Gln Lys His Gly Val Asp Tyr Gly Tyr Cys Tyr Ala
         30                  35                  40 ttc caa tgc tgg tgt gaa ttt ctg aag gat gag aac gtg aag gtc tga       240
Phe Gln Cys Trp Cys Glu Phe Leu Lys Asp Glu Asn Val Lys Val *
     45                  50                  55
```

<210> SEQ ID NO 15
<211> LENGTH: 79
<212> TYPE: PRT
<213> ORGANISM: Artificial Sequence
<220> FEATURE:
<221> NAME/KEY: SIGNAL
<222> LOCATION: (1)...(21)
<223> OTHER INFORMATION: Codon biased nucleotide sequence encoding Aam1.
      Codon biased to rice.

<400> SEQUENCE: 15

```
Met Lys Ala Phe Thr Leu Ala Leu Phe Leu Ala Leu Ser Leu Tyr Leu
    -20                 -15                 -10

Leu Pro Asn Pro Ala Ala Asp Val Pro Gly Asn Tyr Pro Leu Asp Ser
 -5                  1               5                  10

Ser Asp Asn Thr Tyr Leu Cys Ala Pro Leu Gly Asp Asn Pro Asp Cys
             15                  20                  25

Ile Lys Ile Cys Gln Lys His Gly Val Asp Tyr Gly Tyr Cys Tyr Ala
         30                  35                  40

Phe Gln Cys Trp Cys Glu Phe Leu Lys Asp Glu Asn Val Lys Val
     45                  50                  55
```

<210> SEQ ID NO 16
<211> LENGTH: 79
<212> TYPE: PRT
<213> ORGANISM: Artificial Sequence
<220> FEATURE:
<223> OTHER INFORMATION: SPAam1 sporamin signal and Aam1
<220> FEATURE:
<221> NAME/KEY: SIGNAL
<222> LOCATION: (1)...(21)

```
<400> SEQUENCE: 16

Met Lys Ala Phe Thr Leu Ala Leu Phe Leu Ala Leu Ser Leu Tyr Leu
    -20                 -15                 -10

Leu Pro Asn Pro Ala Ala Asp Val Pro Gly Asn Tyr Pro Leu Asp Ser
 -5                  1               5                  10

Ser Asp Asn Thr Tyr Leu Cys Ala Pro Leu Gly Asp Asn Pro Asp Cys
             15                  20                  25

Ile Lys Ile Cys Gln Lys His Gly Val Asp Tyr Gly Tyr Cys Tyr Ala
         30                  35                  40

Phe Gln Cys Trp Cys Glu Phe Leu Lys Asp Glu Asn Val Lys Val
     45                  50                  55

<210> SEQ ID NO 17
<211> LENGTH: 249
<212> TYPE: DNA
<213> ORGANISM: Artificial Sequence
<220> FEATURE:
<223> OTHER INFORMATION: Codon biased nucleotide sequence encoding Aam1.
      Codon biased to Streptomyces coelicolor.
<220> FEATURE:
<221> NAME/KEY: CDS
<222> LOCATION: (73)...(249)
<220> FEATURE:
<221> NAME/KEY: sig_peptide
<222> LOCATION: (1)...(72)
<223> OTHER INFORMATION: BAA signal peptide

<400> SEQUENCE: 17 atg gcc aac aag cac ctg tcc ctg tcg tta ttc ctg gtc ctc ctc ggc      48
Met Ala Asn Lys His Leu Ser Leu Ser Leu Phe Leu Val Leu Leu Gly
            -20                 -15                 -10 ctc tcc gcc tcc ctc gcg agc ggt gcc gac gtg cca ggg aac tac ccg      96
Leu Ser Ala Ser Leu Ala Ser Gly Ala Asp Val Pro Gly Asn Tyr Pro
        -5                   1               5 ctg gac agc tcg gac aac acc tac ctg tgc gca ccc ctg ggc gac aac     144
Leu Asp Ser Ser Asp Asn Thr Tyr Leu Cys Ala Pro Leu Gly Asp Asn
     10                  15                  20 ccg gac tgc atc aag atc tgc cag aag cac ggc gtc gac tac ggc tac     192
Pro Asp Cys Ile Lys Ile Cys Gln Lys His Gly Val Asp Tyr Gly Tyr
 25                  30                  35                  40 tgc tac gcg ttc cag tgt tgg tgc gag ttc ctg aag gac gag aac gtc     240
Cys Tyr Ala Phe Gln Cys Trp Cys Glu Phe Leu Lys Asp Glu Asn Val
                 45                  50                  55 aag gtg tga                                                         249
Lys Val *

<210> SEQ ID NO 18
<211> LENGTH: 82
<212> TYPE: PRT
<213> ORGANISM: Artificial Sequence
<220> FEATURE:
<221> NAME/KEY: SIGNAL
<222> LOCATION: (1)...(24)
<223> OTHER INFORMATION: Codon biased nucleotide sequence encoding Aam1.
      Codon biased to Streptomyces coelicolor.

<400> SEQUENCE: 18

Met Ala Asn Lys His Leu Ser Leu Ser Leu Phe Leu Val Leu Leu Gly
            -20                 -15                 -10

Leu Ser Ala Ser Leu Ala Ser Gly Ala Asp Val Pro Gly Asn Tyr Pro
        -5                   1               5

Leu Asp Ser Ser Asp Asn Thr Tyr Leu Cys Ala Pro Leu Gly Asp Asn
     10                  15                  20
```

```
Pro Asp Cys Ile Lys Ile Cys Gln Lys His Gly Val Asp Tyr Gly Tyr
 25                  30                  35                  40

Cys Tyr Ala Phe Gln Cys Trp Cys Glu Phe Leu Lys Asp Glu Asn Val
                 45                  50                  55

Lys Val

<210> SEQ ID NO 19
<211> LENGTH: 82
<212> TYPE: PRT
<213> ORGANISM: Artificial Sequence
<220> FEATURE:
<223> OTHER INFORMATION: BAAAam1 BAA signal and Aam1
<220> FEATURE:
<221> NAME/KEY: SIGNAL
<222> LOCATION: (1)...(24)
<223> OTHER INFORMATION: BAA signal peptide

<400> SEQUENCE: 19

Met Ala Asn Lys His Leu Ser Leu Ser Leu Phe Leu Val Leu Leu Gly
                -20                 -15                 -10

Leu Ser Ala Ser Leu Ala Ser Gly Ala Asp Val Pro Gly Asn Tyr Pro
             -5                   1                   5

Leu Asp Ser Ser Asp Asn Thr Tyr Leu Cys Ala Pro Leu Gly Asp Asn
     10                  15                  20

Pro Asp Cys Ile Lys Ile Cys Gln Lys His Gly Val Asp Tyr Gly Tyr
 25                  30                  35                  40

Cys Tyr Ala Phe Gln Cys Trp Cys Glu Phe Leu Lys Asp Glu Asn Val
                 45                  50                  55

Lys Val

<210> SEQ ID NO 20
<211> LENGTH: 58
<212> TYPE: PRT
<213> ORGANISM: Androctonus amoreuxi

<400> SEQUENCE: 20

Ala Asp Val Pro Gly Asn Tyr Pro Leu Asp Ser Ser Asp Asn Thr Tyr
  1               5                  10                  15

Leu Cys Ala Pro Leu Gly Asp Asn Pro Asp Cys Ile Lys Ile Cys Gln
                 20                  25                  30

Lys His Gly Val Asp Tyr Gly Tyr Cys Tyr Ala Phe Gln Cys Trp Cys
             35                  40                  45

Glu Phe Leu Lys Asp Glu Asn Val Lys Val
     50                  55

<210> SEQ ID NO 21
<211> LENGTH: 479
<212> TYPE: DNA
<213> ORGANISM: Centruroides vittatus
<220> FEATURE:
<221> NAME/KEY: CDS
<222> LOCATION: (117)...(359)
<220> FEATURE:
<221> NAME/KEY: misc_feature
<222> LOCATION: (0)...(0)
<223> OTHER INFORMATION: Ts7
<220> FEATURE:
<221> NAME/KEY: misc_feature
<222> LOCATION: 425, 431, 469
<223> OTHER INFORMATION: n = A,T,C or G

<400> SEQUENCE: 21
```

```
ggccgctcta gaactagtgg atccccccggg ctgcaggaat tcggcacgag acattttacc      60
ataacggtaa aaacgtttct attaatactt tctttagtga aaaaaaactt gaaagt atg     119
                                                              Met
                                                                1 aaa ttc ttc cta att gtg tca ttg gca ata atg tcg tgt ttc atg gaa      167
Lys Phe Phe Leu Ile Val Ser Leu Ala Ile Met Ser Cys Phe Met Glu
      5                  10                  15 atg aaa gaa gta tac gca ggt acg aaa gga aat ttt ccc gtc gat ttt      215
Met Lys Glu Val Tyr Ala Gly Thr Lys Gly Asn Phe Pro Val Asp Phe
         20                  25                  30 caa gga ata ttt tac gaa tgc atc gta tac aat aga tgt gaa cgc gac      263
Gln Gly Ile Phe Tyr Glu Cys Ile Val Tyr Asn Arg Cys Glu Arg Asp
     35                  40                  45 tgc aag tta cat gga tcg agt tat ggc tat tgc tac gct gga gtt tgc      311
Cys Lys Leu His Gly Ser Ser Tyr Gly Tyr Cys Tyr Ala Gly Val Cys
 50                  55                  60                  65 tac tgc gaa ggt tta gct gac gaa gat aaa tat ttc ctg gga atg taa      359
Tyr Cys Glu Gly Leu Ala Asp Glu Asp Lys Tyr Phe Leu Gly Met  *
                 70                  75                  80 tgaaaaaaca atgccgatta aatgtaaaat caatatcgtt attgccctac aataagcgat    419
taatcntttt gngagattaa ccttgggaat aatggttacc taaaaaactn gggaataaaa    479

<210> SEQ ID NO 22
<211> LENGTH: 80
<212> TYPE: PRT
<213> ORGANISM: Centruroides vittatus

<400> SEQUENCE: 22

Met Lys Phe Phe Leu Ile Val Ser Leu Ala Ile Met Ser Cys Phe Met
  1               5                  10                  15

Glu Met Lys Glu Val Tyr Ala Gly Thr Lys Gly Asn Phe Pro Val Asp
                 20                  25                  30

Phe Gln Gly Ile Phe Tyr Glu Cys Ile Val Tyr Asn Arg Cys Glu Arg
             35                  40                  45

Asp Cys Lys Leu His Gly Ser Ser Tyr Gly Tyr Cys Tyr Ala Gly Val
 50                  55                  60

Cys Tyr Cys Glu Gly Leu Ala Asp Glu Asp Lys Tyr Phe Leu Gly Met
 65                  70                  75                  80

<210> SEQ ID NO 23
<211> LENGTH: 243
<212> TYPE: DNA
<213> ORGANISM: Centruriodes vittatus

<400> SEQUENCE: 23
atgaaattct tcctaattgt gtcattggca ataatgtcgt gtttcatgga atgaaagaa      60 gtatacgcag gtacgaaagg aaattttccc gtcgatttc aaggaatatt ttacgaatgc    120
atcgtataca atagatgtga acgcgactgc aagttacatg gatcgagtta tggctattgc    180
tacgctggag tttgctactg cgaaggttta gctgacgaag ataaatattt cctgggaatg    240
taa                                                                  243

<210> SEQ ID NO 24
<211> LENGTH: 57
<212> TYPE: PRT
<213> ORGANISM: Centruroides vittatus

<400> SEQUENCE: 24
```

```
Gly Thr Lys Gly Asn Phe Pro Val Asp Phe Gln Gly Ile Phe Tyr Glu
  1               5                  10                  15

Cys Ile Val Tyr Asn Arg Cys Glu Arg Asp Cys Lys Leu His Gly Ser
             20                  25                  30

Ser Tyr Gly Tyr Cys Tyr Ala Gly Val Cys Tyr Cys Glu Gly Leu Ala
         35                  40                  45

Asp Glu Asp Lys Tyr Phe Leu Gly Met
     50                  55

<210> SEQ ID NO 25
<211> LENGTH: 292
<212> TYPE: DNA
<213> ORGANISM: Artificial Sequence
<220> FEATURE:
<223> OTHER INFORMATION: Codon biased nucleotide sequence encoding Ts7.
      Codon biased to Streptomyces coelicolor.
<220> FEATURE:
<221> NAME/KEY: CDS
<222> LOCATION: (73)...(292)
<220> FEATURE:
<221> NAME/KEY: sig_peptide
<222> LOCATION: (1)...(72)
<223> OTHER INFORMATION: BAA signal sequence

<400> SEQUENCE: 25 atg gcg aac aag cac ctc tcc ctg tcg ctg ttc ctc gtc ctg ctg ggc      48
Met Ala Asn Lys His Leu Ser Leu Ser Leu Phe Leu Val Leu Leu Gly
            -20                 -15                 -10 ctg tcg gcg agc ctc gcc tcc ggc ggg acc aag ggc aac ttc ccg gtc      96
Leu Ser Ala Ser Leu Ala Ser Gly Gly Thr Lys Gly Asn Phe Pro Val
        -5                   1                   5 gac ttc cag ggt atc ttc tac gag tgc atc gtg tac aac cgc tgc gag     144
Asp Phe Gln Gly Ile Phe Tyr Glu Cys Ile Val Tyr Asn Arg Cys Glu
 10                  15                  20 cgg gac tgt aag ctg cac ggc agc tcc tac ggc tac tgc tac gcc ggc     192
Arg Asp Cys Lys Leu His Gly Ser Ser Tyr Gly Tyr Cys Tyr Ala Gly
 25                  30                  35                  40 gtg tgc tac tgc gag ggg ctc gcc gac gaa gac aag tac ttc ctg gga     240
Val Cys Tyr Cys Glu Gly Leu Ala Asp Glu Asp Lys Tyr Phe Leu Gly
                 45                  50                  55 atg taa gac gct ccc cga gcg gct gct tct gtt cat gaa gga ccc tta     288
Met  *  Asp Ala Pro Arg Ala Ala Ala Ser Val His Glu Gly Pro Leu
                 60                  65                  70 cat t                                                                292
His

<210> SEQ ID NO 26
<211> LENGTH: 81
<212> TYPE: PRT
<213> ORGANISM: Artificial Sequence
<220> FEATURE:
<223> OTHER INFORMATION: BAATs7 BAA signal and Ts7
<220> FEATURE:
<221> NAME/KEY: SIGNAL
<222> LOCATION: (1)...(24)
<223> OTHER INFORMATION: BAA

<400> SEQUENCE: 26

Met Ala Asn Lys His Leu Ser Leu Ser Leu Phe Leu Val Leu Leu Gly
            -20                 -15                 -10

Leu Ser Ala Ser Leu Ala Ser Gly Gly Thr Lys Gly Asn Phe Pro Val
        -5                   1                   5

Asp Phe Gln Gly Ile Phe Tyr Glu Cys Ile Val Tyr Asn Arg Cys Glu
 10                  15                  20
```

-continued

```
Arg Asp Cys Lys Leu His Gly Ser Ser Tyr Gly Tyr Cys Tyr Ala Gly
 25              30                  35                  40

Val Cys Tyr Cys Glu Gly Leu Ala Asp Glu Asp Lys Tyr Phe Leu Gly
                 45                  50                  55

Met

<210> SEQ ID NO 27
<211> LENGTH: 64
<212> TYPE: PRT
<213> ORGANISM: Adroctonus amoreuxi

<400> SEQUENCE: 27

Val Arg Asp Gly Tyr Ile Ala Asp Ala Gly Asn Cys Gly Tyr Thr Cys
 1               5                  10                  15

Val Ala Asn Asp Tyr Cys Asn Thr Glu Cys Thr Lys Asn Gly Ala Glu
                 20                  25                  30

Ser Gly Tyr Cys Gln Trp Phe Gly Arg Tyr Gly Asn Ala Cys Trp Cys
             35                  40                  45

Ile Lys Leu Pro Asp Lys Val Pro Ile Lys Val Pro Gly Lys Cys Asn
         50                  55                  60
```